United States Patent [19]
Kumagai

[11] Patent Number: 6,081,809
[45] Date of Patent: Jun. 27, 2000

[54] INTERPOLATIVE METHOD AND SYSTEM FOR PRODUCING MEDICAL CHARTS AND MONITORING AND RECORDING PATIENT CONDITIONS

[76] Inventor: Yasuo Kumagai, 344-29 Imachi, Imaich-shi, Tochigi-Ken, 321-12, Japan

[21] Appl. No.: 08/819,860

[22] Filed: Mar. 17, 1997

Related U.S. Application Data

[63] Continuation-in-part of application No. 08/510,665, Aug. 3, 1995, Pat. No. 5,812,983.

[51] Int. Cl.⁷ .................................................. G06F 17/30
[52] U.S. Cl. ............................ 707/104; 707/503; 705/3; 705/2
[58] Field of Search ..................... 707/104, 10, 506–510, 707/1–4, 503; 705/2, 3

[56] References Cited

U.S. PATENT DOCUMENTS

| | | | |
|---|---|---|---|
| 5,319,777 | 6/1994 | Perez | 707/10 |
| 5,337,405 | 8/1994 | Lindauer et al. | 395/764 |
| 5,410,704 | 4/1995 | Norden-Paul et al. | 395/671 |
| 5,682,526 | 10/1997 | Smokoff et al. | 707/104 |
| 5,812,983 | 9/1998 | Kumagai | 705/3 |

*Primary Examiner*—Hosain T. Alam
*Attorney, Agent, or Firm*—Lane, Aitken & McCann

[57] ABSTRACT

A computer system referred to as a Database Management System with Nested Time Axes (DBMS with NTA), which cooperates with a Computed Medical File and Chart System (CMFCS), employs data processing techniques to solve problems related to data collection and analysis in daily medical practice. It reconstructs irregularly or regularly collected data and places it into a database table with a standardized time axis acceptable for the CMFCS. Multiple records of an original database at irregular intervals are correlated to a progeny database with a standardized time axis by averaging, maximizing and minimizing. The DBMS with NTA consists of several database tables, each of which has a relational time axis, and corresponding programs to reconstruct a root database table to a progeny database table in hierarchical order. The DBMS with NTA cooperating with the CMFCS allows users to automatically create computer displayed medical charts from the short range view (microscopic view) via the standard view to the long range view (wide angle view) serially using several different time axes. It also creates a computer displayed medical chart showing the maximum and minimum values along with the average value in the same time axis.

13 Claims, 47 Drawing Sheets

The function, @CELLPOINTER("ADDRESS") returns the absolute address of the current cell pointer.

The function, @LEFT(COLCAL_1,3) which returns the left 3 characters from the absolute address of the current cell pointer to extract the current column label.

patient's I.D.
patient's name
93/12/19
93/12/19 ~ 12/25   1

| DATE | WK | data item | data item 2 |
|---|---|---|---|
|  |  |  |  |
| 93/12/19 ~12/25 | 1 |  |  |
| 12/26 ~ 01/01 | 2 |  |  |
| 01/02 ~ 01/08 | 3 |  |  |
| 01/09 ~ 01/15 | 4 |  |  |
| 01/16 ~ 01/22 | 5 |  |  |
| 01/23 ~ 01/29 | 6 |  |  |
| 01/30 ~ 02/05 | 7 |  |  |
| 02/06 ~ 02/12 | 8 |  |  |
| 02/13 ~ 02/19 | 9 |  |  |
| 02/20 ~ 02/26 | 10 |  |  |
| 02/27 ~ 03/05 | 11 |  |  |
| 03/06 ~ 03/12 | 12 |  |  |
| 03/13 ~ 03/19 | 13 |  |  |
| 03/20 ~ 03/26 | 14 |  |  |
| 03/27 ~ 04/02 | 15 |  |  |
| 04/03 ~ 04/09 | 16 |  |  |
| 04/10 ~ 04/16 | 17 |  |  |
| 04/17 ~ 04/23 | 18 |  |  |
| 04/24 ~ 04/30 | 19 |  |  |
| 05/01 ~ 05/07 | 20 |  |  |
| 05/08 ~ 05/14 | 21 |  |  |
| 05/15 ~ 05/21 | 22 |  |  |
| 05/22 ~ 05/28 | 23 |  |  |
| 05/29 ~ 06/04 | 24 |  |  |
| 06/05 ~ 06/11 | 25 |  |  |
| 06/12 ~ 06/18 | 26 |  |  |
| 06/19 ~ 06/25 | 27 |  |  |

FIG.2 patient's I.D.
patient's name
　　　93/12/19
　　　　12/20 mon　　1

| DATE | WK | HSP | data item | data item |2
|---|---|---|---|---|
| | | | | |
| | | | | |
| 93/12/19 | sun | 1 | | |
| 12/20 | mon | 2 | | |
| 12/21 | tue | 3 | | |
| 12/22 | wed | 4 | | |
| 12/23 | thr | 5 | | |
| 12/24 | fri | 6 | | |
| 12/25 | sat | 7 | | |
| 12/26 | sun | 8 | | |
| 12/27 | mon | 9 | | |
| 12/28 | tue | 10 | | |
| 12/29 | wed | 11 | | |
| 12/30 | thr | 12 | | |
| 12/31 | fri | 13 | | |
| 01/02 | sat | 14 | | |
| 01/03 | sun | 15 | | |
| 01/04 | mon | 16 | | |
| 01/05 | tue | 17 | | |
| 01/06 | wed | 18 | | |
| 01/07 | thr | 19 | | |
| 01/08 | fri | 20 | | |
| 01/09 | sat | 21 | | |
| 01/10 | sun | 22 | | |
| 01/11 | mon | 23 | | |
| 01/12 | tue | 24 | | |
| 01/13 | wed | 25 | | |
| 01/14 | thr | 26 | | |
| 01/15 | fri | 27 | | |

FIG.3 patient's I.D.
patient's name
93/12/26

| DATE | HSP | TRIM | data item | data item 2 |
|---|---|---|---|---|
|  |  |  |  |  |
| 93/12/26 | 1 | M |  |  |
|  |  | E |  |  |
|  |  | N |  |  |
| 93/12/27 | 2 | M |  |  |
|  |  | E |  |  |
|  |  | N |  |  |
| 93/12/28 | 3 | M |  |  |
|  |  | E |  |  |
|  |  | N |  |  |
| 93/12/29 | 4 | M |  |  |
|  |  | E |  |  |
|  |  | N |  |  |
| 93/12/30 | 5 | M |  |  |
|  |  | E |  |  |
|  |  | N |  |  |
| 93/12/31 | 6 | M |  |  |
|  |  | E |  |  |
|  |  | N |  |  |
| 94/01/01 | 7 | M |  |  |
|  |  | E |  |  |
|  |  | N |  |  |
| 94/01/02 | 8 | M |  |  |
|  |  | E |  |  |
|  |  | N |  |  |
| 94/01/03 | 9 | M |  |  |
|  |  | E |  |  |
|  |  | N |  |  |

FIG.4 patient's I.D.
patient's name
93/12/26

| DATE | HSP | HOUR | data item1 | data item |
|---|---|---|---|---|
| 93/12/26 | 1 | 1 | | |
| 93/12/26 | 1 | 2 | | |
| 93/12/26 | 1 | 3 | | |
| 93/12/26 | 1 | 4 | | |
| 93/12/26 | 1 | 5 | | |
| 93/12/26 | 1 | 6 | | |
| 93/12/26 | 1 | 7 | | |
| 93/12/26 | 1 | 8 | | |
| 93/12/26 | 1 | 9 | | |
| 93/12/26 | 1 | 10 | | |
| 93/12/26 | 1 | 11 | | |
| 93/12/26 | 1 | 12 | | |
| 93/12/26 | 1 | 13 | | |
| 93/12/26 | 1 | 14 | | |
| 93/12/26 | 1 | 15 | | |
| 93/12/26 | 1 | 16 | | |
| 93/12/26 | 1 | 17 | | |
| 93/12/26 | 1 | 18 | | |
| 93/12/26 | 1 | 19 | | |
| 93/12/26 | 1 | 20 | | |
| 93/12/26 | 1 | 21 | | |
| 93/12/26 | 1 | 22 | | |
| 93/12/26 | 1 | 23 | | |
| 93/12/26 | 1 | 24 | | |
| 93/12/27 | 2 | 1 | | |
| 93/12/27 | 2 | 2 | | |
| 93/12/27 | 2 | 3 | | |

FIG.5 patient's name

00/01/01 ****

| DATE | HSP | BS 7:00 | BS 21:00 | Hb-Alc | UV | diet | Daonil |
|---|---|---|---|---|---|---|---|
| 93/10/25 | 1 | | | 11.1 | | | |
| 93/10/26 | 2 | | | | 2000 | 1600 | |
| 93/10/27 | 3 | | | | 1800 | | |
| 93/10/28 | 4 | 295.9 | | | 1600 | | |
| 93/10/29 | 5 | | | | 1250 | | |
| 93/10/30 | 6 | 283.3 | 383.7 | | 1700 | | |
| 93/10/31 | 7 | | | | | | |
| 93/11/01 | 8 | | | | 1350 | | |
| 93/11/02 | 9 | 260.4 | 366.3 | 10.5 | | | |
| 93/11/03 | 10 | | | | 1100 | | |
| 93/11/04 | 11 | | | | | | |
| 93/11/05 | 12 | | | | 1000 | | |
| 93/11/06 | 13 | | | | 1200 | | |
| 93/11/07 | 14 | | | | 1150 | | |
| 93/11/08 | 15 | 221.6 | 284.1 | | 950 | | |

FIG.6 patient's name

| 148 | | 00/01/01 | +B147+ | (+C147+C149)/2 | (+D147+D149)/2 | (+E147+E149)/2 | | +G147 | +H147 |
|---|---|---|---|---|---|---|---|---|---|
| 149 | DATE | HSP | D | BS 7:00 | BS 21:00 | Hb-Alc | UV | diet | Daonil |
| 150 | | | | | | | | | |
| 151 | 93/10/25 | | 1 | | | | | | |
| 152 | 93/10/26 | | 2 | | | (+E151+D153)/2 | 2000 | 1600 | |
| 153 | 93/10/27 | | 3 | | | (+E152+D154)/2 | 1800 | +G152 | |
| 154 | 93/10/28 | | 4 | 295.9 | | (+E153+D155)/2 | 1600 | +G153 | |
| 155 | 93/10/29 | | 5 | (+C154+C156)/2 | | (+E154+D156)/2 | 1250 | +G154 | |
| 156 | 93/10/30 | | 6 | 283.3 | 383.7 | | 1700 | +G155 | |
| 157 | 93/10/31 | | 7 | (+C156+C158)/2 | (+D156+D158)/2 | (+E155+D157)/2 | | +G156 | |
| 158 | 93/11/01 | | 8 | (+C157+C159)/2 | (+D157+D159)/2 | (+E156+D158)/2 | 1350 | +G157 | |
| 159 | 93/11/02 | | 9 | 260.4 | 366.3 | (+E157+D159)/2 | | +G158 | |
| 160 | 93/11/03 | | 10 | (+C159+C161)/2 | (+D159+D161)/2 | (+E159+D161)/2 | 1100 | +G159 | |
| 161 | 93/11/04 | | 11 | (+C160+C162)/2 | (+D160+D162)/2 | (+E160+D162)/2 | | +G160 | |
| 162 | 93/11/05 | | 12 | (+C161+C163)/2 | (+D161+D163)/2 | (+E161+E163)/2 | 1000 | +G161 | |
| 163 | 93/11/06 | | 13 | (+C162+C164)/2 | (+D162+D164)/2 | (+E162+D164)/2 | 1200 | +G162 | |
| 164 | 93/11/07 | | 14 | (+C163+C165)/2 | (+D163+D165)/2 | (+E163+D165)/2 | 1150 | +G163 | |
| 165 | 93/11/08 | | 15 | 221.6 | 284.1 | (+E164+D166)/2 | 950 | +G164 | |

FIG. 7

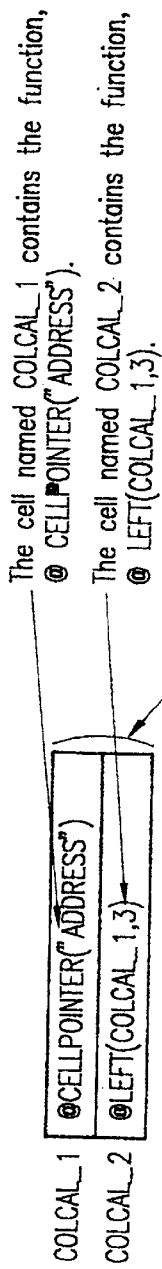

The cell named COLCAL_1 contains the function, @CELLPOINTER("ADDRESS").

The cell named COLCAL_2 contains the function, @LEFT(COLCAL_1,3).

The cells, COLCAL_1 and COLCAL_2 are named COLCAL1_2.

FIG. 14

The function, @CELLPOINTER("ADDRESS") returns the absolute address of the current cell pointer.

The function, @LEFT(COLCAL_1,3) which returns the left 3 characters from the absolute address of the current cell pointer to extract the current column label.

| COLCAL_1 | $D$153 |
| COLCAL_2 | $D$ |

FIG. 15

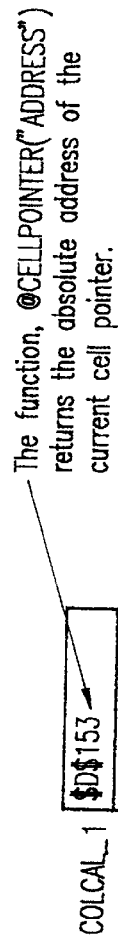

91. The cells, COLCAL1_2 are recalculated.
92. The current column label in COLCAL_2 is combined with 148, and the result is written to HOKAN_3 which is the cell name of step 94 of the program list. The cell is locally unprotected.
93 to 95. The formula written in the row 148 of the current column is copied to the area named HOKAN. This macro command could be same as {menu}c$D$148~HOKAN~. In this case, the program has to rewrite $D$148 according to the current column.

| 91 | {recalc COLCAL1_2} |
| 92 | {let HOKAN_3,COLCAL_2&+"148":value} |
| 93 | {menu}c |
| 94 | $D$148 |
| 95 | ~HOKAN~ |

The cell of step 94 is named HOKAN_3 and locally unprotected.

FIG. 16

| | 100 | 100 |
|---|---|---|
| +$TOP+($CURRENT−$TOP)/(@CELL("row",B12..B12)−@CELL("row",$TOP)) | 111.111111111 |
| +$TOP+($CURRENT−$TOP)/(@CELL("row",B13..B13)−@CELL("row",$TOP)) | 122.222222222 |
| +$TOP+($CURRENT−$TOP)/(@CELL("row",B14..B14)−@CELL("row",$TOP)) | 133.333333333 |
| +$TOP+($CURRENT−$TOP)/(@CELL("row",B15..B15)−@CELL("row",$TOP)) | 144.444444444 |
| +$TOP+($CURRENT−$TOP)/(@CELL("row",B16..B16)−@CELL("row",$TOP)) | 155.555555556 |
| +$TOP+($CURRENT−$TOP)/(@CELL("row",B17..B17)−@CELL("row",$TOP)) | 166.666666667 |
| +$TOP+($CURRENT−$TOP)/(@CELL("row",B18..B18)−@CELL("row",$TOP)) | 177.777777778 |
| +$TOP+($CURRENT−$TOP)/(@CELL("row",B19..B19)−@CELL("row",$TOP)) | 188.888888889 |
| | 200 | 200 |

FIG.29

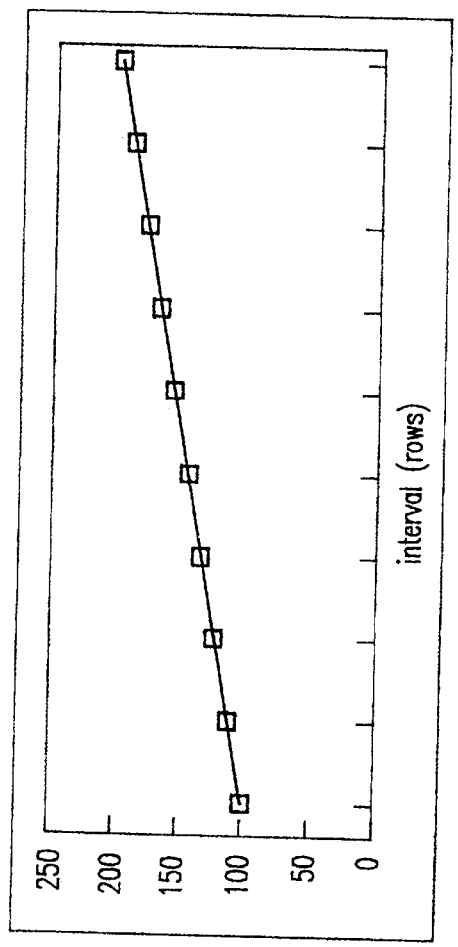

FIG.30

ORIGINAL_DATA

| PT_ID | DATE | TIME | DATE_TIME | BP_SYS | BP_DIA | PR | BT | respiration | O2_inhal | O2_sat |
|---|---|---|---|---|---|---|---|---|---|---|
| 785476 | 94/07/18 | 15:00 | 34533.625 | 140 | 80 | 110 | 38.1 | | | |
| 785476 | 94/07/18 | 19:00 | 34533.7917 | 162 | 70 | 132 | 38.2 | mask | 2 | 92 |
| 785476 | 94/07/19 | 06:00 | 34534.25 | 150 | 98 | 128 | 37.7 | mask | 2 | 91 |
| 785476 | 94/07/19 | 12:15 | 34534.5104 | 152 | 82 | 104 | 38 | | | |
| 785476 | 94/07/19 | 12:45 | 34534.5313 | 200 | 110 | 178 | | | | |
| 785476 | 94/07/19 | 13:20 | 34534.5556 | 182 | 110 | 155 | | | | |
| 785476 | 94/07/19 | 14:20 | 34534.5972 | 150 | 90 | 150 | | | | |
| 785476 | 94/07/19 | 16:00 | 34534.6667 | 170 | 110 | 123 | 38 | | | |
| 785476 | 94/07/19 | 19:00 | 34534.7917 | 170 | 102 | 128 | 38 | mask | 4 | 92 |
| 785476 | 94/07/19 | 19:50 | 34534.8264 | 180 | 110 | 152 | 37.1 | ventilator | 60 | 85 |
| 785476 | 94/07/19 | 22:00 | 34534.9167 | 148 | 100 | 187 | | ventilator | 100 | |
| 785476 | 94/07/19 | 22:10 | 34534.9236 | 98 | 60 | 165 | | ventilator | 100 | 94 |
| 785476 | 94/07/19 | 22:40 | 34534.9444 | 100 | 50 | 98 | 37.2 | | | |
| 785476 | 94/07/19 | 23:30 | 34534.9792 | 130 | 84 | 96 | 37 | ventilator | 100 | 98 |
| 785476 | 94/07/20 | 03:35 | 34535.149 | 132 | 80 | 85 | 36.9 | ventilator | 100 | 98 |
| 785476 | 94/07/20 | 04:10 | 34535.174 | 140 | 100 | 160 | | | | |
| 785476 | 94/07/20 | 06:00 | 34535.25 | 112 | 70 | 128 | 36.5 | | | |
| 785476 | 94/07/20 | 08:00 | 34535.3333 | 150 | 90 | 142 | | ventilator | 80 | |
| 785476 | 94/07/20 | 09:00 | 34535.375 | 100 | 60 | 130 | 36.4 | | | |
| 785476 | 94/07/20 | 11:30 | 34535.4792 | 132 | 60 | 94 | 36.4 | | | |
| 785476 | 94/07/20 | 14:30 | 34535.6042 | 130 | 80 | 103 | | | | |
| 785476 | 94/07/20 | 16:10 | 34535.6736 | 110 | 70 | 120 | 37.4 | | | |
| 785476 | 94/07/20 | 16:25 | 34535.684 | | | | | ventilator | 80 | 97 |
| 785476 | 94/07/20 | 17:00 | 34535.7083 | 142 | 80 | 92 | | ventilator | 60 | 97 |
| 785476 | 94/07/20 | 17:45 | 34535.7396 | 150 | 80 | 110 | | | | |
| 785476 | 94/07/20 | 18:00 | 34535.75 | 138 | 86 | 103 | 37.6 | ventilator | 60 | 97 |
| 785476 | 94/07/20 | 21:00 | 34535.875 | | | | 37.7 | ventilator | 60 | 97 |

FIG32

| H_AVG_ACCUM | | | | | | | | | | | |
|---|---|---|---|---|---|---|---|---|---|---|---|
| PT_ID | DATE | TIME_FIRST | TIME_LAST | BP_SYS | BP_DIA | PR | BT | respiration | O2_inhal | O2_sat | |

FIG.36

ORIGINAL_DATA

| PT_ID | DATE | TIME | DATE_TIME | BP_SYS | BP_DIA | PR |
|---|---|---|---|---|---|---|
| 785476 | 94/07/18 | 15:00 | 34533.625 | 140 | 80 | |
| 785476 | 94/07/18 | 19:00 | 34533.79167 | 162 | 70 | |
| 785476 | 94/07/19 | 06:00 | 34534.25 | 150 | 98 | |
| 785476 | 94/07/19 | 12:15 | 34534.51042 | 152 | 82 | |
| 785476 | 94/07/19 | 12:45 | 34534.53125 | 200 | 110 | |
| 785476 | 94/0 | 13:20 | 34534.5555 | 182 | 110 | |

A EXAMPLE OF H_TIMETBL

| H_DAY_CTR | | 0 |
| H_FIRST | 94/07/18 | 34533 |
| H_DATE | | 34533 |
| H_LAST | 94/08/18 | 34564 |
| H_HOUR_CTR | | 18 |
| H_START | | 34533.75 |
| H_END | | 34533.79167 |

FORMULAE OF H_TIMETBL

| H_DAY_CTR | | 0 |
| H_FIRST | 94/07/18 | @ROUND(M2,0) |
| H_DATE | | +H_FIRST+H_DAY_CTR |
| H_LAST | 94/08/18 | @ROUND(M4,0) |
| H_HOUR_CTR | | 18 |
| H_START | | +H_DATE+(H_HOUR_CTR)/24 |
| H_END | | +H_DATE+(H_HOUR_CTR+1)/24 |

FIG.37

FORMULAE OF H_CRL_AREA

| PT_ID | DATE_TIME |
|---|---|
| 785476 | +DATE_TIME>H_START#AND#+DATE_TIME<=H_END |

FORMULAE OF H_CALC

| PT_ID | DATE | TIME_START | TIME_END | BP_SYS | BP_DIA |
|---|---|---|---|---|---|
| +$H_PIT_PTID | +$H_START | +$H_START | +$H_END | @COUNT(E$11..E$40) | @COUNT(F$11..F$40) @COUNT |
| +$H_PIT_PTID | +$H_START | +$H_START | +$H_END | @AVG(E$11/E$40) | @AVG(F$11/F$40) @AVG(G$ |
| +$H_ PTID | START | START | ND | | |

A EXAMPLE OF H_AVG_ACCUM

| PT_ID | DATE | TIME_START | TIME_END | BP_SYS | BP_DIA | P |
|---|---|---|---|---|---|---|
| 785476 | 94/07/18 | 14:00 | 15:00 | 140 | 80 | |
| 785476 | 94/07/18 | 18:00 | 19:00 | 162 | 70 | |
| 785476 | 94/07/19 | 05:00 | 06:00 | 150 | 98 | |
| 785476 | 94/07/19 | 12:00 | 13:00 | 176 | 96 | |
| | | 13:0 | 14:0 | 1 | | |

FIG.38

A EXAMPLE OF
H_AVG_ACCUM

| PT_ID | DATE | TIME_START | TIME_END | BP_SYS | BP_DIA | P |
|---|---|---|---|---|---|---|
| 785476 | 94/07/18 | 14:00 | 15:00 | 140 | 80 | |
| 785476 | 94/07/18 | 18:00 | 19:00 | 162 | 70 | |
| 785476 | 94/07/19 | 05:00 | 06:00 | 150 | 98 | |
| 785476 | 94/07/19 | 12:00 | 13:00 | 176 | 96 | |

A EXAMPLE OF
T_TIMETBL

| T_DAY_CTR | | 5 |
|---|---|---|
| T_FIRST | 94/07/18 | 34533 |
| T_DATE | | 34538 |
| T_LAST | 94/08/18 | 34564 |
| T_TRL_CTR | | 0 |
| T_START | | 34538 |
| T_END | | 34538.33333 |

FORMULAE OF
T_TIMETBL

| T_DAY_CTR | | 5 |
|---|---|---|
| T_FIRST | 94/07/18 | @ROUND(M2,0) |
| T_DATE | | +T_FIRST+T_DAY_CTR |
| T_LAST | 94/08/18 | @ROUND(M4,0) |
| T_TRL_CTR | | 18 |
| T_START | | +T_DATE+(T_TRL_CTR)/3 |
| T_END | | +T_DATE+(T_TRL_CTR+1)/3 |

FORMULAE OF T_CRL_AREA

| PT_ID | TIME_START |
|---|---|
| 785476 | +TIME_START>T_START#AND#+TIME_START<=T-END |

FORMULAE OF T_CALC

| PT_ID | DATE | TIME_START | TIME_END | BP_SYS | BP_DIA |
|---|---|---|---|---|---|
| $+T_OUT_PTID | +$T_START | +$T_START | +$T_END | @COUNT(E$11.E$40) | @COUNT(F$11.F$40) |
| $+T_OUT_PTID | +$T_START | +$T_START | +$H_END | @AVG(E$11.E$40) | @AVG(F$11.F$40) |
| PTID | START | | NO | | |

A EXAMPLE OF T_AVG_ACCUM

| PT_ID | DATE | TIME_START | TIME_END | BP_SYS | BP_DIA | PR |
|---|---|---|---|---|---|---|
| 785476 | 94/07/18 | 08:00 | 16:00 | 140 | 80 | |
| 785476 | 94/07/18 | 16:00 | 00:00 | 162 | 70 | |
| 785476 | 94/07/19 | 00:00 | 08:00 | 150 | 98 | 142 |
| 785476 | 94/07/19 | 08:00 | 16:00 | 169.5 | 101.5 | 1 |
| | | 16:00 | | 145 | | |

A EXAMPLE OF
H_AVG_ACCUM

| PT_ID | DATE | TIME_START | TIME_END | BP_SYS | BP_DIA | PR |
|---|---|---|---|---|---|---|
| 785476 | 94/07/18 | 14:00 | 15:00 | 140 | 80 | |
| 785476 | 94/07/18 | 18:00 | 19:00 | 162 | 70 | |
| 785476 | 94/07/19 | 05:00 | 06:00 | 150 | 98 | |
| 785476 | 94/07/19 | 12:00 | 13:00 | 176 | 96 | |
| 785476 | | | 14:00 | 180 | | |

A EXAMPLE OF
D_TIMETBL

| D_DAY_CTR | | 15 |
|---|---|---|
| D_FIRST | | 34533 |
| D_LAST | | 34564 |
| D_FINAL | | 31 |
| D_START | | 34548 |
| D_END | | 34549 |

| | 94/07/18 |
| | 94/08/18 |

FORMULAE OF
D_TIMETBL

| D_DAY_CTR | | 15 |
|---|---|---|
| D_FIRST | 94/07/18 | @ROUND(M2,0) |
| D_LAST | 94/08/18 | @ROUND(M3,0) |
| D_FINAL | | @DATEDIF(+D_FIRST,+D_LAST,"d") |
| D_START | | +D_FIRST+D_DAY_CTR |
| D_END | | +D_START+1 |

FIG.41

FORMULAE OF
D_CRL_AREA

| PT_ID | TIME_START |
|---|---|
| 785476 | +TIME_START>+D_START#AND#+TIME_START<=+D_END |

FORMULAE OF D_CALC

| PT_ID | MONTH | SUNDAY | DATE | BP_SYS | BP_DIA |
|---|---|---|---|---|---|
| +$D_OUT_PTID | @MONTH(+D51) | +$D_START-@VLOOK+$D_START | +$D_START | @COUNT(E$11..E$42) | @COUNT(F$11..F$42) |
| +$D_OUT_PTID | @MONTH(+D51) | +$D_START-@VLOOK+$D_START | +$D_START | @AVG(E$11..E$42) | @AVG(F$11..F$42) |
| | @MONTH( | | START | E$11..E$42) | |

A EXAMPLE OF
D_AVG_ACCUM

| PT_ID | MONTH | SUNDAY | DATE | BP_SYS | BP_DIA | P |
|---|---|---|---|---|---|---|
| 785476 | 7 | 94/07/17 | 94/07/18 | 151.00 | 75.00 | 12 |
| 785476 | 7 | 94/07/17 | 94/07/19 | 155.50 | 95.50 | 13 |
| 785476 | 7 | 94/07/17 | 94/07/20 | 128.18 | 77.82 | 113 |
| 785476 | 7 | 94/07/17 | 94/07/21 | 150.00 | 85.75 | 98 |
| 785476 | 7 | 94/07/17 | 94/07/22 | 173.50 | 92.25 | 86 |
| | | 94/07 | | 166.32 | 93 | 73 |

FIG. 42

A EXAMPLE OF
D_AVG_ACCUM

| PT_ID | MONTH | SUNDAY | DATE | BP_SYS | BP_DIA | PR |
|---|---|---|---|---|---|---|
| 785476 | 7 | 94/07/17 | 94/07/18 | 151.00 | 75.00 | 12 |
| 785476 | 7 | 94/07/17 | 94/07/19 | 155.50 | 95.50 | 13 |
| 785476 | 7 | 94/07/17 | 94/07/20 | 128.18 | 77.82 | 11 |
| 785476 | 7 | 94/07/17 | 94/07/21 | 150.00 | 85.75 | 96 |
| 78 | 7 | 9 | 94/07/22 | 173.50 | 92.25 | 86 |

A EXAMPLE OF
W_TIMETBL

| W_WEEK_CTR | 5 | |
|---|---|---|
| W_FIRST | 94/07/19 | 94/07/19 |
| W_LAST | 94/08/18 | 94/08/18 |
| W_FINAL | | 5 |
| W_START | | 94/08/21 |
| W_END | | 94/08/20 |

TABLE OF W_MOD

| W_MOD | |
|---|---|
| 0 | 0 |
| 1 | 6 |
| 2 | 5 |
| 3 | 4 |
| 4 | 3 |
| 5 | 2 |
| 6 | 1 |

FORMULAE OF
W_TIMETBL

| W_WEEK_CTR | 5 |
|---|---|
| W_FIRST | @ROUND(M2,0) |
| W_LAST | @ROUND(M3,0) |
| W_FINAL | @TRUNC((@DAYS(+W_FIRST,+W_LAST,1)/7)+1 |
| W_START | +W_FIRST−@VLOOKUP(@MOD(+W_FIRST,7),W_MOD,1)+W_WEEK_CTR*7 |
| W_END | +W_LAST+@VLOOKUP(@MOD(W_LAST,7),W_MOD,2) |

FIG. 43

FORMULAE OF W_CRL_AREA

| PT_ID | DATE |
|---|---|
| 785476 | +DATE>=W_START#AND#+DATE<=+W_END |

FORMULAE OF W_CALC

| PT_ID | WK_NO | SUNDAY | SATURDAY | BP_SYS | BP_DIA | PR |
|---|---|---|---|---|---|---|
| +$W_OUT_PTID | +$W_WEEK_CTR+1 | +$W_START | +$W_START+6 | @COUNT(E$11..E$17) | @COUNT(F$11..F$17) | @COUNT |
| +$W_OUT_PTID | +$W_WEEK_CTR+1 | +$W_START | +$W_START+6 | @AVG(E$11..E$17) | @AVG(F$11..F$17) | @AVG(G$ |
| +$W | +$W_WEEK | +$W_START | START+6 | (E$11..E$17) | (F$11..F$17) | |

A EXAMPLE OF W_AVG_ACCUM

| PT_ID | WK_NO | SUNDAY | SATURDAY | BP_SYS | BP_DIA | PR |
|---|---|---|---|---|---|---|
| 785476 | 1 | 94/07/17 | 94/07/23 | 154.09 | 86.55 | 10 |
| 785476 | 2 | 94/07/24 | 94/07/30 | 150.16 | 79.73 | 6 |
| 785476 | 3 | 94/07/31 | 94/08/06 | 155.28 | 75.07 | 66 |
| 785476 | 4 | 94/08/07 | 94/08/13 | 147.14 | 71.14 | 53 |

FIG.44

A EXAMPLE OF
D_AVG_ACCUM

| PT_ID | MONTH | SUNDAY | DATE | BP_SYS | BP_DIA | PR |
|---|---|---|---|---|---|---|
| 785476 | 7 | 94/07/17 | 94/07/18 | 151.00 | 75.00 | 12 |
| 785476 | 7 | 94/07/17 | 94/07/19 | 155.50 | 95.50 | 13 |
| 785476 | 7 | 94/07/17 | 94/07/20 | 128.18 | 77.82 | 11 |
| 785476 | 7 | 94/07/17 | 94/07/21 | 150.00 | 85.75 | 96 |
|  | 7 |  | 94/07/22 | 173.50 | 92.25 | 86 |

A EXAMPLE OF
M_TIMETBL

| M_MONTH_CTR | 13 |
| M_FIRST | 34533 | 94/07/18 |
| M_LAST | 34898 | 95/07/18 |
| M_FINAL | 13 |
| M_START | 20 |
| M_END | 21 |

FORMULAE OF
M_TIMETBL

| M_MONTH_CTR | 13 |
| M_FIRST | @ROUND(M2,0) | 94/07/18 |
| M_LAST | @ROUND(M3,0) | 95/07/31 |
| M_FINAL | @DATEDIF(+M_FIRST,+M_LAST,"m")+1 |
| M_START | @MONTH(M_FIRST)+M_MONTH_CTR |
| M_END | +M_START+1 |

FIG.45

FORMULAE OF
M_CRL_AREA

| PT_ID | MONTH |
|---|---|
| 785476 | +MONTH>=+M_START#AND#+MONTH<=+M_END |

FORMULAE OF
M_CALC

| PT_ID | MONTH | BP_SYS | BP_DIA | PR | BT | respira |
|---|---|---|---|---|---|---|
| +$M_OUT_PTID | +$M_START | @COUNT(E$11..E$42) | @COUNT(F$11..F$42) | @COUNT(G$11..G$42) | @COUNT(H$11..H$42) | @COUNT(I$ |
| +$M_OUT_PTID | +$M_START | @AVG(E$11..E$42) | @AVG(F$11..F$42) | @AVG(G$11..G$42) | @AVG(H$11..H$42) | @AVG($ |
| +$M_OUT_PTID | +$M_START | (E$11..E$42) | (F$11..F$42) | (G$11..G$42) | (H$11..H$42) | ($ |

A EXAMPLE OF
M_AVG_ACCUM

| PT_ID | MONTH | BP_SYS | BP_DIA | PR | BT | respiration |
|---|---|---|---|---|---|---|
| 785476 | 7 | 151.89 | 82.30 | 80.99 | 36.70 | 0. |
| 785476 | 8 | 154.36 | 71.45 | 63.19 | 36.35 | 0. |

FIG.46

| directory table | no 1 | no 2 | no 3 | no 4 |
|---|---|---|---|---|
| DIRECTRY | C:\LABO | I:\NURSE | I:\NURSE | |
| FILE_NAME | LABO_DAT.DBF | PT_DATA.DBF | DRUG.DBF | |
| CONDITION | COND_1 | COND_1 | COND_1 | |
| OUTPUT | OUT 1 | OUT 2 | OUT 3 | |

FIG.53

| date calculation table | |
|---|---|
| DAY_CTR | 3 |
| FIRST_DATE | @DATE(93,10,25) |
| START_DATE | 93/10/30 |
| DATA_DATE | START_DATE+DAY_CTR |
| CHA_DATE | 93/11/02 |
| TODAY | @INT(@NOW) |
| DATE DIF | @DATEDIF(FIRST DATE,DATA DATE,"d") |

FIG.54

FIG.55 condition area

| KBFR | | 10.5 | |
|---|---|---|---|
| | date | | |
| =000002 | =93/11/02 | | | output area

| out 1 | | out 2 | | out 3 | |
|---|---|---|---|---|---|
| BS 7 | BS 21 | Hb A1c | UV | diet | Daonil |
| 260.4 | 366.3 | 10.5 | | | | the cellpointer moves down 9 rows (fixed)

| HSP | BS 7 | BS 21 | Hb A1c | UV | diet | Daonil |
|---|---|---|---|---|---|---|
| 1 | | | | | | |
| 2 | | | | | | |
| 3 | | | | | | |
| 4 | 295.9 | | | | | |
| 5 | | | | | | |
| 6 | | 283.3 | | | | |
| 7 | | 383.7 | 11.1 | | | |
| 8 | | | | | | |
| 9 | 260.4 | 366.3 | | | | | the cellpointer still moves down the row of @datedif(FIRST DATE, DATA DATE, "d")

this cell is named 'CURRENT'

| 93/10/25 | | | |
|---|---|---|---|
| 10/26 | tue | | 1 |
| DATE | WK | | |
| 93/10/25 | mon | | 1 |
| 10/26 | tue | | 2 |
| 10/27 | wed | | 3 |
| 10/28 | thr | | 4 |
| 10/29 | fri | | 5 |
| 10/30 | sat | | 6 |
| 10/31 | sun | | 7 |
| 11/01 | mon | | 8 |
| 11/02 | tue | | 9 |

CPK — PMDM without interstitial pneumonia

| HSP DAY | patient 1 | patient 2 | patient 3 | patient 4 | patient 5 | patient 6 |
|---|---|---|---|---|---|---|
| 1 | | | | | | |
| 2 | | | | | | |
| 3 | 1943 | | | | | |
| 4 | | 1596 | | | | |
| 5 | | | | | | |
| 6 | | | | 2818 | | |
| 7 | | | 7565 | | 354 | |
| 8 | | | | | | |
| 9 | | 1993 | 9075 | | | |
| 10 | | | | 2246 | | |
| 11 | | | | | | 339 |
| 12 | | 1107 | 6573 | 1550 | 250 | |
| 13 | | | | | | |
| 14 | | | | | | |
| 15 | | | | 739 | | |
| 16 | 1568 | | | | | 158 |
| 17 | | | 1750 | | 98 | |
| 18 | | 981 | | | | |
| 19 | | | | 219 | | |
| 20 | | | | | | |
| 21 | | | | | | 65 |
| 22 | 229 | | | 136 | | |
| 23 | | | | | | |
| 24 | | | | | | |

FIG.56

INTERPOLATIVE METHOD AND SYSTEM FOR PRODUCING MEDICAL CHARTS AND MONITORING AND RECORDING PATIENT CONDITIONS

The following application is a continuation-in-part of presently U.S. application Ser. No. 08/510,665, filed Aug. 3, 1995, now U.S. Pat. No. 5,812,983 issued Sep. 22, 1998.

FIELD OF THE INVENTION

This invention relates to a computer software system for medical use, and more particularly, to a system which collects, organizes and integrates various kinds of medical data collected on a regular or irregular basis from different sources such as doctors, nurses, laboratories, drug companies and hospitals.

BACKGROUND OF THE INVENTION

U.S. application Ser. No. 08/510,665, now U.S. Pat. No. 5,812,983, relates to a computer software system of spread sheets and charts specialized for medical use, and more particularly, a data processing system which integrates and displays various kinds of medical data collected at irregular intervals from different sources such as doctors, nurses, laboratory personnel, and others.

The system of the '665 application is useful because tremendous amounts of data are generated in daily medical practice. Based on this data, doctors make decisions about how to treat and care for a patient. The system of the '665 application assists doctors by integrating this data and more effectively presenting it to doctors and other medical staff.

In medical practice, there are various kinds of data coming from different sources. Some of the data, for example, blood pressure, pulse rate, body temperature and urine volume, are observed by nurses several times everyday. Others like biochemical or serological tests are measured by a laboratory once a week, month, or even year. Furthermore, whether a patient is in the acute or chronic phase of an illness may affect the frequency of data collection.

Human factors exacerbate this irregularity. Sometimes a patient does not visit his or her doctor on the appointment date, and consequently, the necessary tests are not taken. There are considerable differences among doctors in the style of clinical testing and treatment of patients' problems. Clinical data may be easily missed by human error or a complicated hospital system.

In the prior art, computer systems which were developed for integration of medical information have not acquired the flexibility to fulfill the essential needs of a daily medical practice. Apart from computer systems, there have been only a few attempts to create more efficient medical information systems than the traditional handwritten medical charts or nurses' records. As explained in the '665 application, Dr. Weed of Case Western Reserve University proposed a Problem Oriented Medical Record (POMR) system in 1969. *Medical Records, Medical Education, and Patient Care*, Lawrence L. Weed, Press of Case Western Reserve University, 1969. According to Dr. Weed's proposal, a POMR includes a flowsheet as well as problem list, patient's database, and follow up notes. A problem list is a list of each patient's problem related to the patient's illness. A flowsheet is a list of parameters that medical personnel monitor over an extended time period for patients (e.g., blood sugar level, urine volume, etc.). A flowsheet of each problem list shows changes over time for selected clinical and therapeutic data for each patient's problem.

The CMFCS of the '665 application uses the idea of a POMR, but the CMFCS solves the problem of irregularly collected data by using real data to interpolate and fill in missing data.

Medical information almost always has several important properties such as patient identification, time, date, data field, and data itself. In the past it has been difficult to properly handle the time properties of medical information in computer systems, but relatively easy to handle other ones. As previously stated, one of the major reasons for this difficulty is the fact that most medical data is collected at irregular intervals.

In the typical clinical course, the times at which medical information is collected is irregular, thereby causing gaps in the medical data. The Computed Medical File and Chart System (CMFCS) of application No. '665 was developed to overcome the difficulties related to the gaps in medical information.

However, the CMFCS alone does not completely solve the problems related to the irregular collection of medical data. Although any time axis can be chosen for the rows of the flowsheet of the CMFCS as long as each row represents the same time interval, more than one piece of datum may exist at a single cell in a given row. For example, multiple readings of body temperature, pulse rate, or blood pressure are taken in a single day.

Because of these multiple readings, the time units associated with particular medical information may have different time axes—for example continuous monitoring, hourly, three times per day, daily, weekly, monthly, yearly or others. Therefore, a patient's medical charts should also have multiple flowsheets which correspond to the multiple time axes. These multiple flowsheets should be summarized and nested in an hierarchical order, and the CMFCS could then follow and view the clinical course of the patient's lifetime with the required detail. In prior systems, paper-based or computer-based patient record systems could not offer this kind of flexibility or detail.

SUMMARY OF THE INVENTION

The present invention is titled "Data Base Management System With Nested Time Axes" and is referenced by the abbreviation "DBMS with NTA". The DBMS with NTA works in conjunction with the Computed Medical File Chart System (CMFCS) of U.S. patent application Ser. No. 08/510,665, now U.S. Pat. No. 5,812,983, to overcome the above-described difficulties of daily medical practice. The CMFCS consists of a modified flowsheet of a Problem Oriented Medical Record (POMR), a program referred to as Perception-Data_entry-Interpolation-Calculation unit (the PDIC unit) and related programs, and computer displayed medical charts.

The modified flowsheet of the CMFCS has a standardized time scale represented by rows of the flowsheet. Depending on the clinical problem, hourly, daily, weekly, monthly, or other time scales can be chosen. The columns of the modified flowsheet are selected to obtain the most comprehensive graphic charts relating to the patient's problem. They include mostly the vital signs, laboratory data, and methods of therapy. Each column consists of the cell which contains the prototype formula for interpolation, the cell which contains the column title, the cell which contains the subtitle and the cells reserved for data entry.

The PDIC unit is the main component of the CMFCS and it consists of several parts and subroutines. When the operator opens a patient's file of the CMFCS, the modified flow sheet of POMR is displayed on the computer's screen. When the file is opened the first time, the cell pointer is placed at the cell address where the row and the column are frozen as the titles. However, if data has been previously input into the file, the cell pointer is placed at the last cell in which data was entered before the file was saved. The operator then moves the cell pointer to the position of the current cell in the flow sheet where data is to be entered and presses [control]+[D] on the keyboard to start the program of the PDIC system. At this point, the naming subroutine names the current cell (CURRENT), and the program mimics the key operation [end]+[down]. The cell to where the cell pointer jumps is named BOTTOM and the cell pointer returns to CURRENT. The program also mimics the key operation [end]+[up]. The cell to where the cell pointer jumps by this operation is named TOP and the cell pointer returns to CURRENT. According to the relation of the rows of these cells, the perception subroutine recognizes the position of the current cell in the column, and the subroutine decides how to interpolate between the currently entered data and the previously entered data, or how to erase cells containing interpolated data that is no longer accurate.

No interpolation is necessary if there are no empty rows separating the new data and the previously entered data. Interpolation is required if new data is entered into the modified flow sheet of the POMR by the operator, there is a cell containing real data above the new data, and there are one or more empty cells between the new data and the real data. Likewise, interpolation is required if new data is entered, there is real data below the new data, and there are one or more empty cells between the new data and the real data. If no real data exists before or after the new data, the remainder of the cells in the column will have no values in them, and no interpolation is done for these cells.

In some instances, previously interpolated data has to be erased. This is necessary when the operator erases a piece of real data, and previously interpolated data is above or below the erased real data. If a piece of real data is erased (for example, because it is in error), interpolated data which was calculated using that erroneous real data either is not needed any more, or it should be recalculated.

In the interpolation subroutine, each cell between the current cell and the cell of the preceding real data (i.e., the top cell) or each cell between the current cell and the cell of the following real data (i.e., the bottom cell) is interpolated in a predefined manner. The system calculates the position of the current column and copies the prototype formula of the current column to each cell in the interpolation range. The addresses of the copied formula are automatically adjusted to each row by Lotus 1-2-3. In one embodiment, the formula includes repeatedly determining for each interpolated cell an average of the preceding neighboring cell and the following neighboring cell. In another embodiment, a gradient between two points (representing two cells) may be calculated. If the neighboring cell averaging method is used, the recalculation subroutine recalculates the average several hundred times and gets a virtual linear line between cells with real or known data. These interpolation methods are mostly used for expressing the changes in clinical parameters, such as laboratory tests or vital signs. Line charts with or without a multiple Y-axis are suitable for this purpose. For the presentation of other clinical parameters like the dosage of drugs or daily dietary intake, the interpolation method of the second embodiment and bar charts would be more suitable. In the prototype formula for drug dosage or daily dietary intake, each interpolated cell is just the same as the one preceding neighboring cell since these dosages and intakes do not change from day to day until the doctor orders such a change. Depending on the nature of the data or method of presentation in the visual chart, interpolation is not always necessary.

The displayed medical charts of the CMFCS are designed so that therapeutic data as well as clinical data are simultaneously shown on the same chart with the same time scale so that people can easily grasp changes in the clinical data and the influence of therapies. In addition to quantitative data, qualitative data like message notes could be shown on these charts. As the technology of multimedia progresses, methods embodying and showing graphical data like X ray films or endoscopic pictures on these charts can be developed.

The CMFCS is more powerful in a client server system of a computer network. Data stored in a server database management system (DBMS) is automatically selected and reconstructed in the flowsheet by the PDIC unit modified to perform this function (the modified PDIC unit). In this situation, while the server DBMS manages data from multiple entry sources, the client CMFCS extracts data from external data bases stored in the server DBMS, and reconstructs the data in the modified flow sheet of POMR. One of the features of the CMFCS is that retrospective data as well as current data can be reconstructed in the same manner.

The worksheet of the modified flowsheet of the CMFCS is automatically and serially linked to external databases in different locations according to a directory table. The patients' data in the different external databases is extracted according to the data items in an output area, which are the same as the column titles of the modified flowsheet, and are located several rows above it. The extracted data is then reconstructed in the flowsheet by the modified PDIC unit.

Consequently, the use of CMFCS in medical studies or drug trials is most beneficial. Most medical studies are the observations of changes of given subjects over time. In clinical studies, observations on predefined time would be a rigorous obligation or serious limitation. It is possible to collect and compare many patients' data of a given data item observed at irregular periods by using the CMFCS because it has a standardized time scale and data interpolated by an appropriate formula. When the spread sheet program has a multi-layer function, the worksheets could be adjusted to the starting date of each patient's specific treatment in order to show more clearly the specific effects of the treatment on certain patients' problems.

The present invention, the DBMS with NTA, acts as a front end module to the CMFCS. It formats irregularly collected data into the proper time units for the CMFCS. The DBMS with NTA operates on a computer network such as one that consists of a file server which acts on a central storage facility for all patients' data, and multiple stations which can access the data. These other stations may be a doctor's office, a nurse station, or departments within a hospital. While the file server executes the DBMS with NTA, the multiple stations which run the CMFCS receive corresponding data from the file server, and reconstruct modified flowsheets of Problem Oriented Medical Record (POMR). The file server works in a nonstop fashion and tables of the DBMS with NTA are automatically opened according to a time schedule.

As explained in detail above, the CMFCS consists of a modified flowsheet of POMR, a program referred to as a Perception-Data_entry-Calculation Unit (the PDIC unit), and computer displayed medical charts. The row and column data structure of commercially available spread sheet programs represents the rows and columns of a modified flowsheet of a POMR. The rows of the flowsheet represent equally spaced time intervals (hours, days, weeks, months, etc.), and the columns represent a particular parameter that is monitored. The PDIC unit is the main component of the CMFCS. It accepts data from the user, places the data at the proper position in the flowsheet, determines the range of cells to use in an interpolation, copies a prototype formula to the range, and interpolates and recalculates the data for those cells.

The DBMS with NTA is organized as several database tables each of which has a relational time axis (e.g., hourly, daily, weekly, etc.) and corresponding programs to move from one database to another in an hierarchical order thereby moving from one time unit to another.

A database used in the DBMS with NTA consists of the fields of the patients' identification, the date and the time when the data is collected, and the data items (clinical parameters). Nurses record patient's ID, date and time, and observed data for each data item, and the system automatically calculates a date-time field. Data items which might be observed are the patient's systolic blood pressure, diastolic blood pressure, pulse rate, body temperature, mode of respiration, $O_2$ administration and saturation of arterial $O_2$.

The DBMS with NTA extracts the records of the database at hourly intervals, calculates the average, maximum and minimum, and reconstructs the database as a database table with an hourly time axis. Subsequently, the database with the hourly time axis serves as a root database table for progeny database tables in the trisection (i.e. three times per day) or daily time axis. The database with the daily time axis serves as the root database table for the progeny database tables in the databases with weekly or monthly time axes. Any other combination of the root and progeny database tables is possible.

Proper database tables are chosen and connected to the corresponding flowsheets of the CMFCS which have the same time axis. The PDIC unit of the CMFCS interpolates and reconstructs the data into the flowsheets. The CMFCS presents multiple charts of medical information with nested time axes. The computer displayed medical charts can show changes of clinical data from short range view (microscopic view) via standard view to long range view (wide angle view) serially using several different time axes. Another method of display using the DBMS with NTA and the CMFCS is simultaneous presentation of the average, maximum and minimum of medical information in a chart.

In the DBMS with NTA, some information is compressed as well as generated. Some important information might be discarded because all data cannot be displayed in the single chart. However, by the presentation of the maximum and minimum value along with the average value in the same time axis, a clinical situation can be presented more accurately. In certain circumstances, the values of standard deviation or standard error could be used instead of the maximum and minimum values.

Accordingly, an object of the invention is to transform a database containing data associated with different time units into a database table with standardized time axes acceptable for use in a computed medical file chart system.

Another object of the invention is to create progeny database tables with nested time axes from a root database table.

A further object of the invention is to allow users to automatically create computer displayed medical charts from a short range view (microscopic view) via standard view to a long range view (wide angle view) serially using several different time axes.

A still further object of the invention is to allow users to automatically create a computer displayed medical chart showing the maximum and minimum values along with the average value in the same time axis.

BRIEF DESCRIPTION OF THE DRAWINGS

FIGS. 2 through 5 illustrate examples of modified flowsheets of a Problem Oriented Medical Record (POMR) employed in the CMFCS.

FIG. 6 is an example illustrating a part of a modified flowsheet for a diabetic patient for use in the CMFCS.

FIG. 7 illustrates the interpolation formulas as well as the real data of the flowsheet of FIG. 6.

FIGS. 14, 15, and 16 illustrate the method used to calculate and decide the current column position.

FIGS. 53 and 54 show the directory table and date calculation table that are used in the program of FIGS. 23 and 24.

FIG. 55 illustrates how to carry and add data to the appropriate position on the flowsheet.

FIG. 56 is an example of a flowsheet showing the collected information on serum creatine phosphokinase (CPK) levels in different patients with polymyositis and dermatomyositis observed during a certain period in the hospital.

FIG. 29 illustrates the gradient formula in use, and the values resulting therefrom.

FIG. 30 is a graph of the interpolated values of FIG. 29.

FIGS. 32 and 33 illustrate a portion of an original database which can serve as input to the DBMS with NTA.

FIGS. 34, 35 and 36 illustrate tables which the DBMS with NTA uses in its processing.

FIGS. 37 and 38 illustrate a portion of ORIGINAL_ DATA and an example for the table H_TIMETBL, formulae of H_TIMETBL, H_CRI_AREA and H_CALC, and an example for the table H_AVG_ACCUM.

FIGS. 39 through 46 illustrate the same arrangement of corresponding worksheets in the TRISECTION, DAY, WEEK and MONTH level.

DESCRIPTION OF A SPECIFIC EMBODIMENT COMPUTED MEDICAL FILE CHART SYSTEM

The present invention relates to a computer system for the medical field which computes data over several time axes. It acts as a front end processor for the computer Medical File Chart System (CMFCS) described in U.S. patent application Ser. No. 08/510,665, now U.S. Pat. No. 5,812,983.

Figure 1:
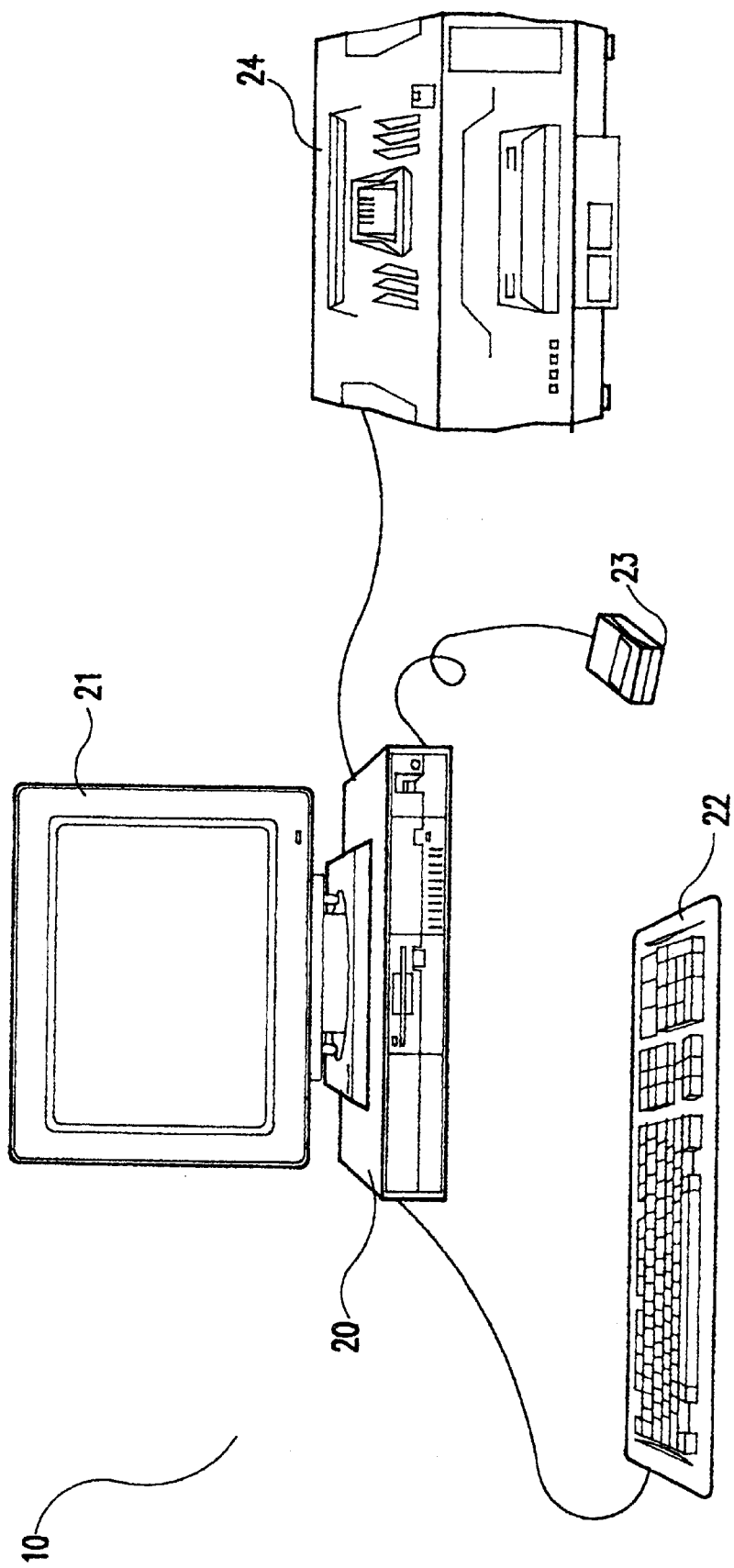
FIG. 1 illustrates a personal computer system which is used in the Computed Medical File and Chart System (CMFCS) and the Database Management System with Nested Time Axes (DBMS with NTA) and which is composed of a central processing unit (CPU), a display, a keyboard, a mouse and a color printer.

As shown in FIG. 1, the CMFCS uses an ordinary personal computer system 10, which comprises a unit 20 within which is a central processing unit (CPU), a display unit 21, a keyboard 22, a mouse 23 and a color printer 24. The computer should be installed with a commercially available spread sheet program such as Lotus 1-2-3 for Windows (1-2-3/Win), Microsoft Excel, Borland Quattro Pro for Windows, or Infomix Wingz. Programs of graphical user interface (GUI) are much better than those of character user interface (CUI). In general, the CMFCS uses the row and column data structure of the Lotus 1-2-3 spreadsheet or other comparable spreadsheet program to represent the rows and columns of a modified flowsheet of a Problem Oriented Medical Record (POMR). The rows of the flowsheet represent equally spaced time intervals (hours, days, weeks, months, etc.), and the columns represent a particular parameter that is monitored.

Figure 8:
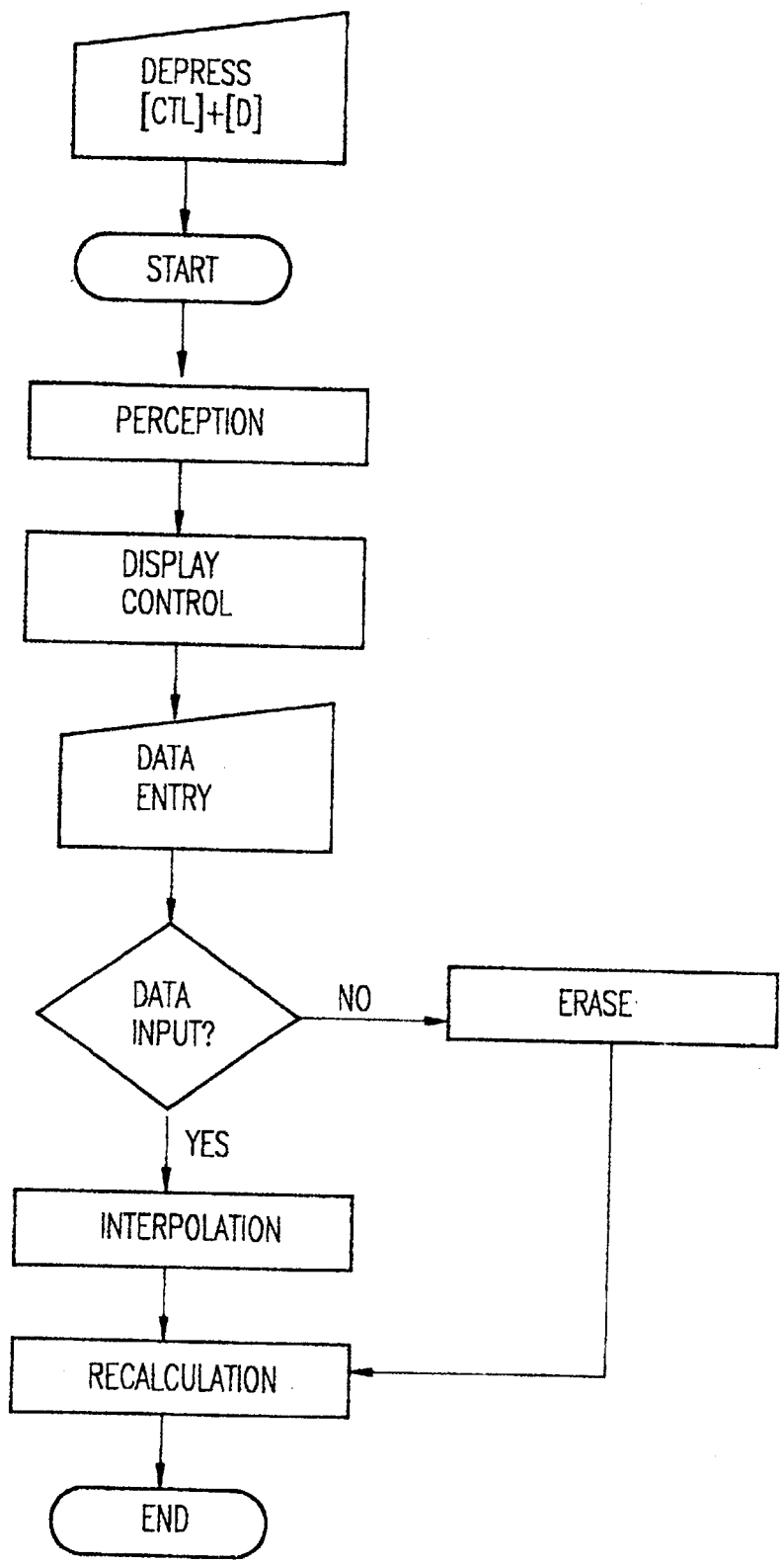
FIG. 8 is a flowchart of the software of the Perception-Data_entry-Interpolation-Calculation unit (the PDIC unit) used in the CMFCS.

The CMFCS comprises in part a program written in the macro language of Lotus 1-2-3 which carries out the interpolation and recalculation of the values for the flowsheet. This macro is referred to as the Perception-Data_entry-Interpolation-Calculation unit (PDIC unit). The PDIC unit accepts data from the user, places that data in a buffer and subsequently in the current cell, determines the range of cells to use in the interpolation, copies a prototype formula to the range, and interpolates and recalculates the data for those cells (see FIG. 8).

FIGS. 2 through 5 illustrate several flowsheets, each set up for the entry of data on a different time interval: FIG. 2 for a weekly basis, FIG. 3 for a daily basis, FIG. 4 for a three times per day basis, and FIG. 5 for an hourly basis. Any scale may be chosen for the rows of the flowsheet as long as each row represents the same time interval.

The flowsheet has a set of data items in each column representing clinical or therapeutic variables for a patient's problem. Doctors or other medical staff select data items to obtain the most pertinent information about the patient's problem. As shown in FIG. 6, the columns include data observed by nurses or other staff, laboratory data, and methods of therapy. In particular, the patient's blood sugar (BS) level, the patient's glucosiliated hemoglobin level, the patient's urine volume (UV), the patient's intake of calories (Diet), and the amount of a drug taken by the patient (Daonil) are recorded for particular hospital days (HSP). The data shown in FIG. 6 represents actual observed data or administered treatments and is called "real data". Each column consists of the cell which contains the prototype formula for interpolation, the cell which contains the column title, the cell which contains the subtitle, and the cells reserved for data entry (FIG. 7).

As to the cells themselves, before any data is entered, they are globally protected. No data can be entered directly into a globally protected cell. Before a user enters data into such a cell, the cell should be locally unprotected. There are two kinds of data—real or interpolated. Real data has a non-hidden cell format, usually general or automatic, while interpolated data has a hidden cell format which is not visible to the user. The PDIC unit determines the range of cells to use in the interpolation, and copies a prototype formula written in the row 148 of each column in the flow sheet to the interpolation range.

The stored formula is written in terms of the rows in relation to each other. When the program copies this formula to the rows of the flowsheet representation in the computer memory which are to be interpolated, Lotus automatically adjusts this formula for the particular row in which it is placed. The system calculates the position of the current column and copies the prototype formula written in the cell of row 148 in the current column to each cell of the interpolation range. For example, in one embodiment of the invention, the interpolation formula averages the preceding cell and the following cell. Referring to FIG. 7, this formula is stored in row 148 as (+C147+C149)/2. The notations C147 and C149 refer to rows 147 and 149 of column C, respectively. When this formula is copied to the rows to be interpolated, it is adjusted accordingly. For example, in FIG. 7, the formula of row 148 (+C147+C149)/2, when copied down to row 158, is adjusted to take the average of the preceding row and next row, i.e., (+C157+C159)/2.

When the operators open a patient's file in the CMFCS through ordinary Lotus 1-2-3's commands, a modified flow sheet of POMR is displayed on the screen. The titles of the columns and rows are frozen at the cell address C151, and when the file is opened for the first time, the cell pointer is placed at this cell address. If data has previously been input into the file, the cell pointer is placed at the last cell in which data was entered before the file was saved.

The operator moves the cell pointer to a position in the flow sheet where data is to be entered, or where data is to be erased, and presses [control]+[D] on keyboard 22 which starts the PDIC unit. At first, the program executes a subroutine named COVER which indicates "execution" on the screen and freezes the screen. Then the program initializes the condition of the worksheets. The program enables global cell protection and sets recalculation iteration to one. The cell protection of a keyboard buffer cell named KBFR is locally unprotected. The cell format at the cell pointer is changed to general, the cell is named CURRENT, and the cell is locally unprotected. In Lotus 1-2-3, the range name is substituted for the address, and this allows Lotus 1-2-3 to act upon the range name rather than the cell addresses.

The program then mimics the key operation of pressing [end]+[down]. If there is a cell with data in the column between the current cell and row 8192 (the last row in Lotus 1-2-3), the cell pointer jumps to that cell, which is identified as bottom, and it is named BOTTOM. If there is no cell with data in the column between the current cell and row 8192, the cell pointer jumps to the cell of row 8192 of the column, which is identified as bottom, and it is named BOTTOM. The cell pointer returns to CURRENT.

In a similar manner, the program mimics the key operation of pressing [end]+[up]. If there is a cell with data in the column between the current cell and row 151 (the row where the column title is frozen), the cell pointer jumps to that cell, which is identified as top, and it is named TOP. If there is no cell with data in the column between the current cell and row 151, the cell pointer jumps to the cell of row 151 of the column, which is identified as top, and it is named TOP. Again the cell pointer returns to CURRENT.

According to the relation of the row of TOP and BOTTOM, the PERCEPTION subroutine then recognizes the position of the current cell in the data sequence of the column. This cell position determines what interpolation subroutine or erase subroutine will be executed following data entry as is described below.

After the PERCEPTION subroutine, the program of the CMFCS enters the DSP CTL (display control) subroutine which improves the visuality of the flow sheet, and the UNCOVER subroutine which unfreezes the screen. A data entry dialog box appears and indicates "Please input new data." If the operator inputs data, which is temporarily stored in the cell named KBFR, then the program executes the interpolation subroutines. If the operator inputs nothing, the program executes the erase subroutines. Again, the program executes the COVER subroutine which indicates "executing" on the panel and freezes the screen.

As explained above, if the user erases real data, interpolated data which was calculated using that real data may have to be erased or interpolated and recalculated again. The program has different erase subroutines and different interpolation subroutines, and the position of the data in the column recognized in the PERCEPTION subroutine determines which subroutine is executed.

Figure 10:
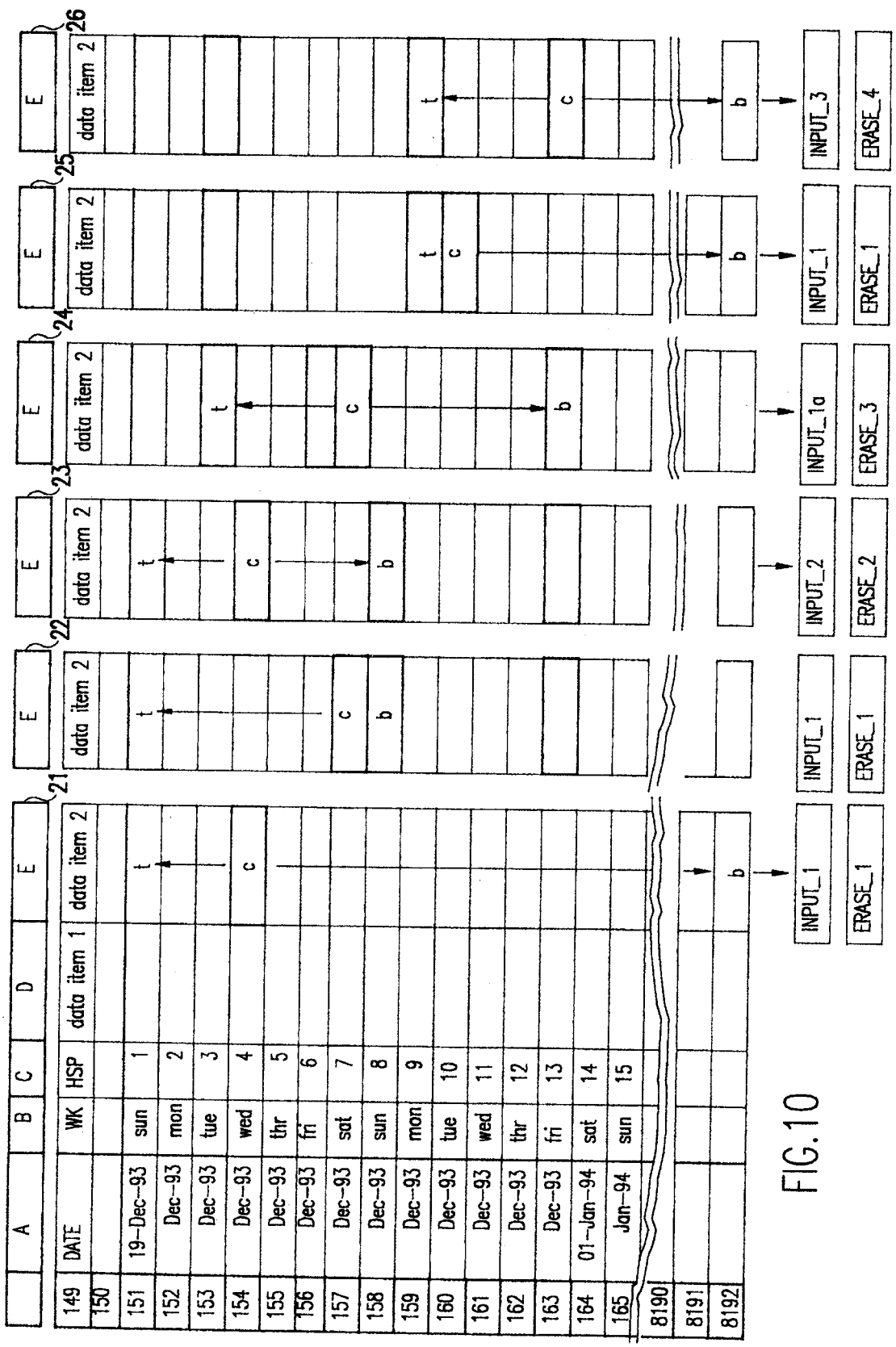
FIG. 10 schematically illustrates the decision logic used in the CMFCS so that a cell recognizes its relative position in the column. It also shows the interpolation and erase subroutines used in each case.
Figure 11:
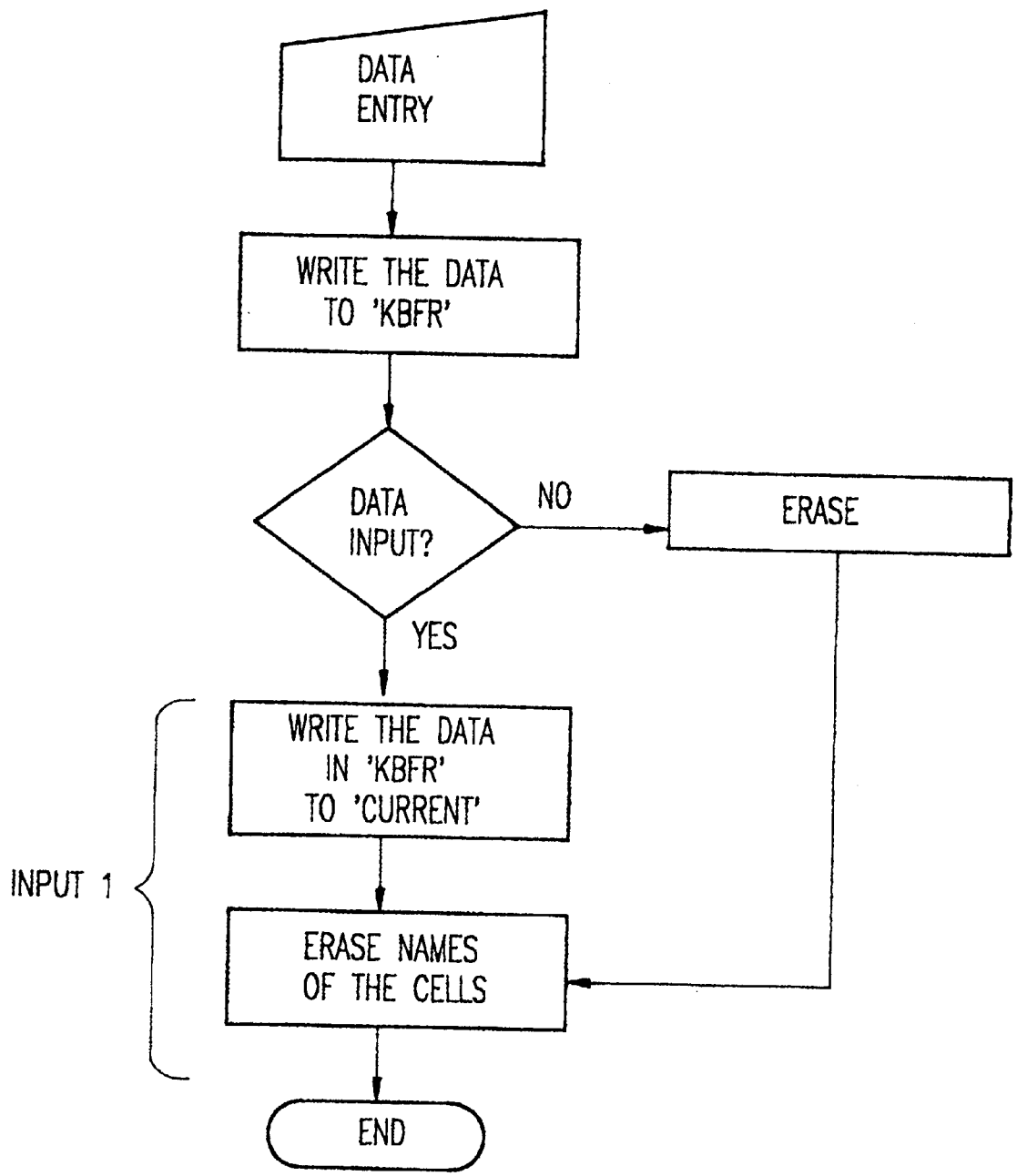
FIGS. 11 and 12 are more detailed flowcharts of routines INPUT_1 and INPUT_3 which include data entry, interpolation and recalculation routines used in the PDIC.
Figure 17:
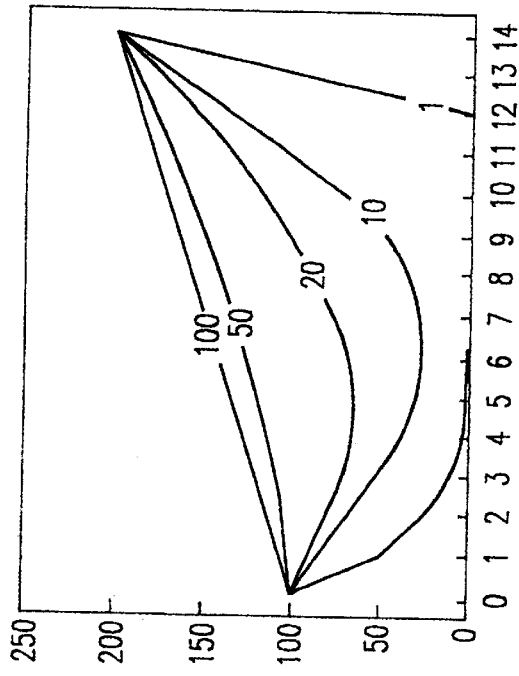
FIGS. 17 and 18 are graphs illustrating how repeated averaging recalculations obtain linear interpolation.

Column 21 in FIG. 10 illustrates an example in which after the execution of the NAMING subroutine, the TOP pointer points to 151, the BOTTOM pointer points to 8192, and the cell pointed to by CURRENT is blank. In this example, the PERCEPTION subroutine will have recognized any data as the first data in the column, and if data were entered, it decides to execute INPUT_1. INPUT_1 is represented in the flow chart of FIG. 11. The INPUT_1 subroutine writes the data that is temporarily stored in KBFR to the cell of the flowsheet to which CURRENT points. The cell is then protected and the CURRENT, BOTTOM and TOP pointer are deleted. Since this is the first piece of data to be entered into the modified flow sheet of the POMR, no interpolation occurs because there is no other data with which to perform an interpolation. If no data is entered (i.e., the user moves the cell pointer to the current cell and presses ENTER without entering any data), the program executes the ERASE 1 subroutine which unprotects the current cell, erases the data in the current cell, protects the current cell once again, and deletes the CURRENT, TOP and BOTTOM pointers as shown in FIG. 17. Program execution then terminates.

In the example represented by column 23 of FIG. 10, after the execution of the NAMING subroutine, the TOP pointer points to row 151, and the BOTTOM pointer points to a cell which is located above row 8192. In this example, the PERCEPTION subroutine will recognize that the position of the CURRENT cell is above (i.e., having a lower cell number than) previously entered data. In this case, if data was entered, the program executes INPUT_2. The INPUT_2 subroutine first checks to see if the row of CURRENT is one above the row of BOTTOM. If it is, the program executes INPUT_1 as shown in column 22 of FIG. 10. Otherwise, INPUT_2 then defines an area of HOKAN extending from one row below CURRENT to one row above BOTTOM. HOKAN is a Japanese word meaning "interpolation". By calculating the position of the current column, the program copies the formula in row 148 of that column to the cells of HOKAN. As explained earlier, the addresses of the copied formula are adjusted to each row. The cell of CURRENT and the cells of HOKAN are then protected, and the names of CURRENT, TOP, BOTTOM and HOKAN are deleted. The program then executes the RECALCULATION or KEISAN subroutine. "KEISAN" means "calculation" in Japanese. In the example of column 23 of FIG. 10, HOKAN extends from row 155 to row 157. In the KEISAN routine, the program globally carries out the interpolation calculations for the entire worksheet. If the user enters no data in the example of column 23 of FIG. 10, the program executes ERASE_2. ERASE_2 erases the data in the current cell and the cells below it until the cell pointer encounters a cell with real data and a non-hidden format. This erasure is necessary since the cells from CURRENT down to BOTTOM contain interpolated data which was interpolated using the data just erased in CURRENT. Because of the erasure of the data in CURRENT, the data in the cells below it are now no longer necessary. When the cell pointer encounters a cell with real data and non-hidden data format, program execution terminates.

Figure 20:
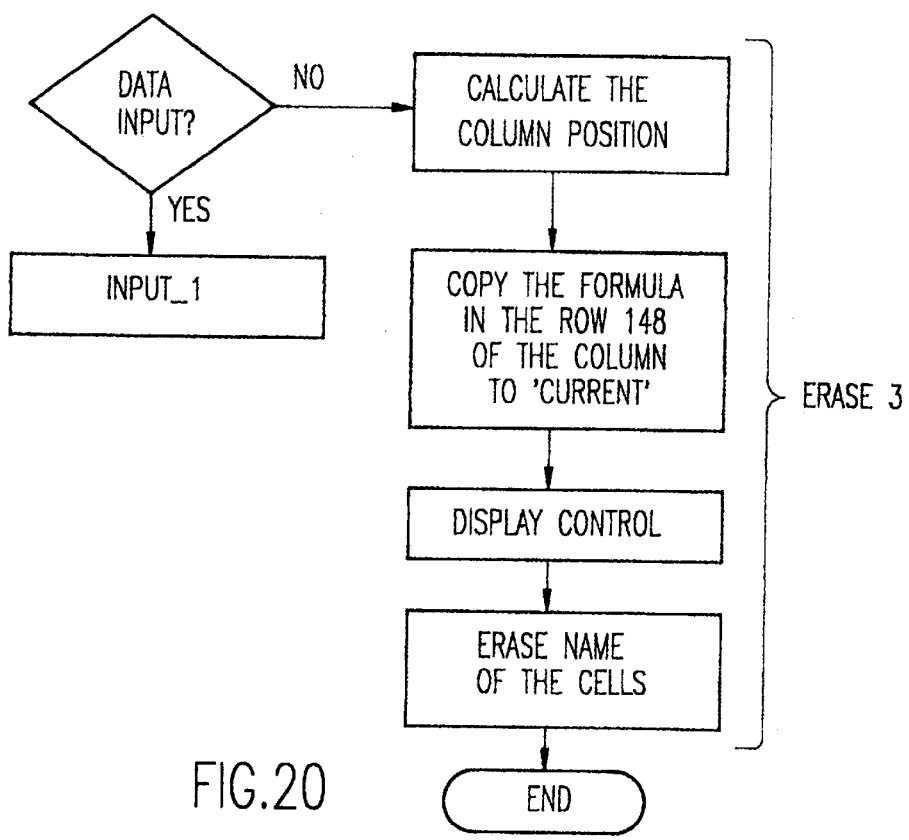

In the example of column 24 of FIG. 10, after the execution of the NAMING subroutine, the TOP pointer points to a cell which is greater than 151, and the BOTTOM pointer points to a cell which is less than 8192. In this situation, the PERCEPTION routine recognizes that the CURRENT cell is between previously entered data. If data is entered, the program executes the INPUT_1a subroutine. Input_1a places the value which is in KBFR into the cell pointed to by CURRENT. INPUT_1a then invokes the KEISAN subroutine which globally recalculates interpolated cells in the entire flowsheet. After multiple recalculations, linear interpolations are obtained between the preceding real data and the CURRENT cell, and between the CURRENT cell and the following real data. In the example of column 24 of FIG. 10, the ERASE_3 subroutine is executed if no data is entered. In this routine, as shown in FIG. 20, the cell is unprotected, the column position of the cell is calculated, and the formula of the row 148 in the column is copied to the cell. Then the subroutine KEISAN is executed to globally recalculate interpolated cells in the entire flowsheet. After multiple recalculation, linear interpolations are obtained between the preceding real data and the CURRENT cell, and between the CURRENT cell and the following real data. The current cell is then protected. The names TOP, BOTTOM and CURRENT are deleted. Program execution then terminates.

Figure 12:
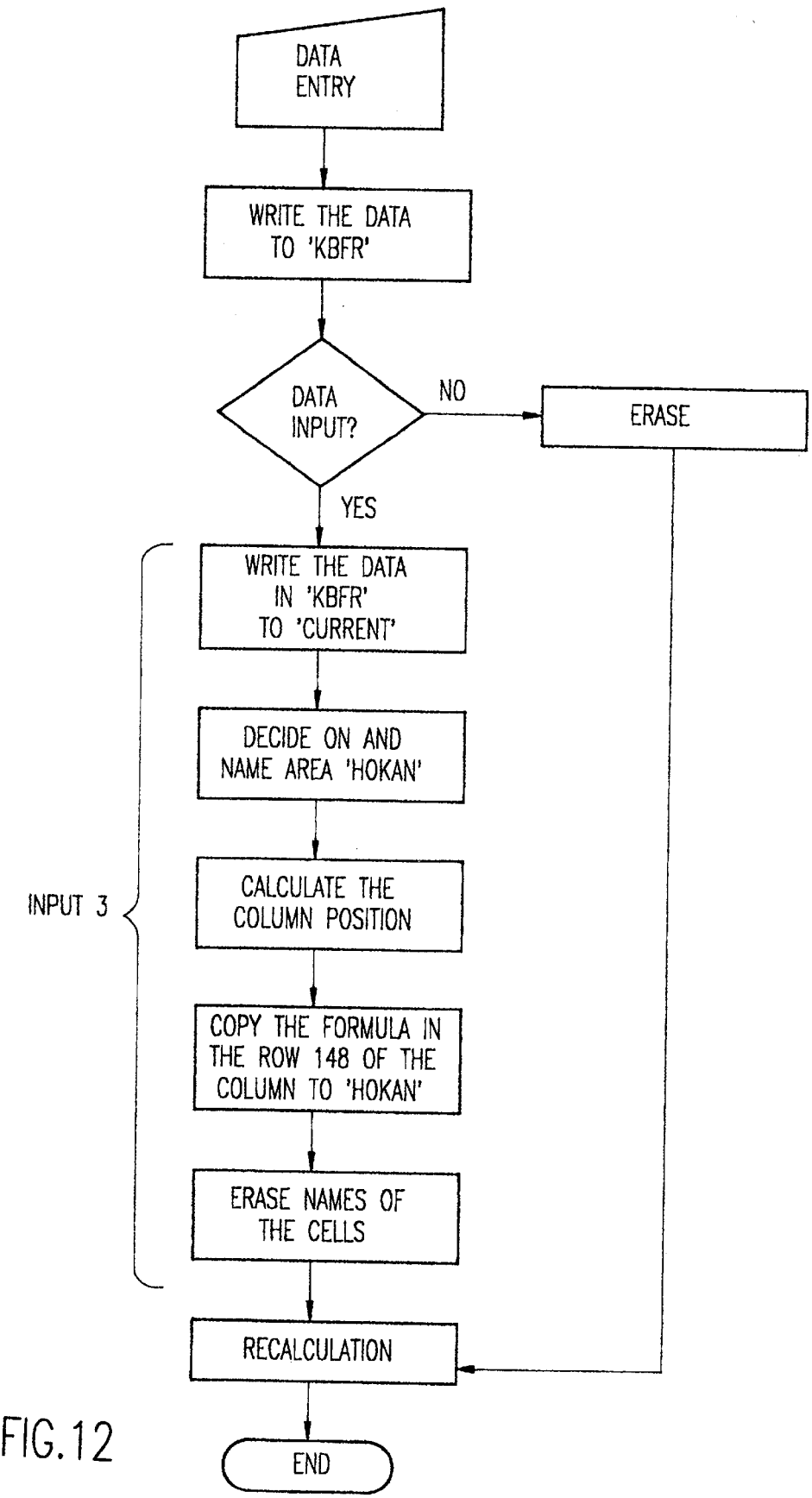
Figure 13:
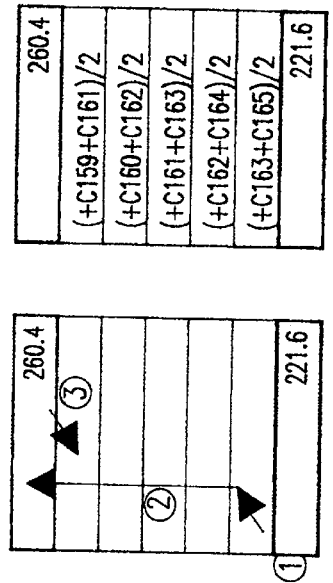
FIG. 13 shows a flowsheet illustrating in graphic fashion how the program defines the rows which it interpolates.

In the example of column 26 of FIG. 10, after the execution of the NAMING subroutine, the TOP pointer points to a cell which is greater than 151, and the BOTTOM pointer points to row 8192. The PERCEPTION subroutine will have recognized the entered data is more than one cell below the previous data. In this case the program executes the INPUT_3 subroutine if data is entered in the current cell. The INPUT_3 subroutine first checks to see if the row of CURRENT is one row below the row of TOP. If it is, the program executes INPUT_1 as shown in column 25 of FIG. 10. ERASE 4 (FIG. 24) is executed if no data is entered in the current cell. If the entered data is more than two rows below the previous data, as shown in FIG. 12, the INPUT_3 subroutine, after the data in KBFR is written to CURRENT, identifies the area between CURRENT and the cell with the last entered data as HOKAN. The INPUT_3 routine then executes the KEISAN subroutine to interpolate the data in HOKAN. FIG. 13 illustrates the cell pointer movement for INPUT_3. The cell pointer steps one cell above the CURRENT, which is the start point (the cell 164 in FIG. 13). The cell pointer then jumps up to the last cell by mimicking the key operation of pressing [end]+[up], and steps down one cell, which is the end point (cell in FIG. 13). The cells of HOKAN are the cells 160 to 164, which are then unprotected. The program recognizes the cell address where the CURRENT cell is (FIG. 14), obtains only the left 3 characters to extract the column label (FIG. 15), and joins the column label with 148 to make the cell address where the prototype formula is written (FIG. 16). Then the prototype formula in the cell is copied to the range HOKAN. As shown in FIG. 13, and as explained earlier, the addresses of the copied formula are adjusted to each row. The cell of CURRENT and the cells of HOKAN are then protected, and the names of CURRENT, TOP, BOTTOM and HOKAN are deleted. Following the erasure of the cell names the program executes the subroutine KEISAN. In the KEISAN subroutine, the value in each cell in which the formula has been copied (the HOKAN cells) is computed in accordance with the formula for each cell in sequence and this process is repeated a large number of times. By repeating the sequential calculation for the cells a large enough number of times, a linear interpolation of the values in each cell is obtained for the cells into which the formula was copied.

Figure 18:
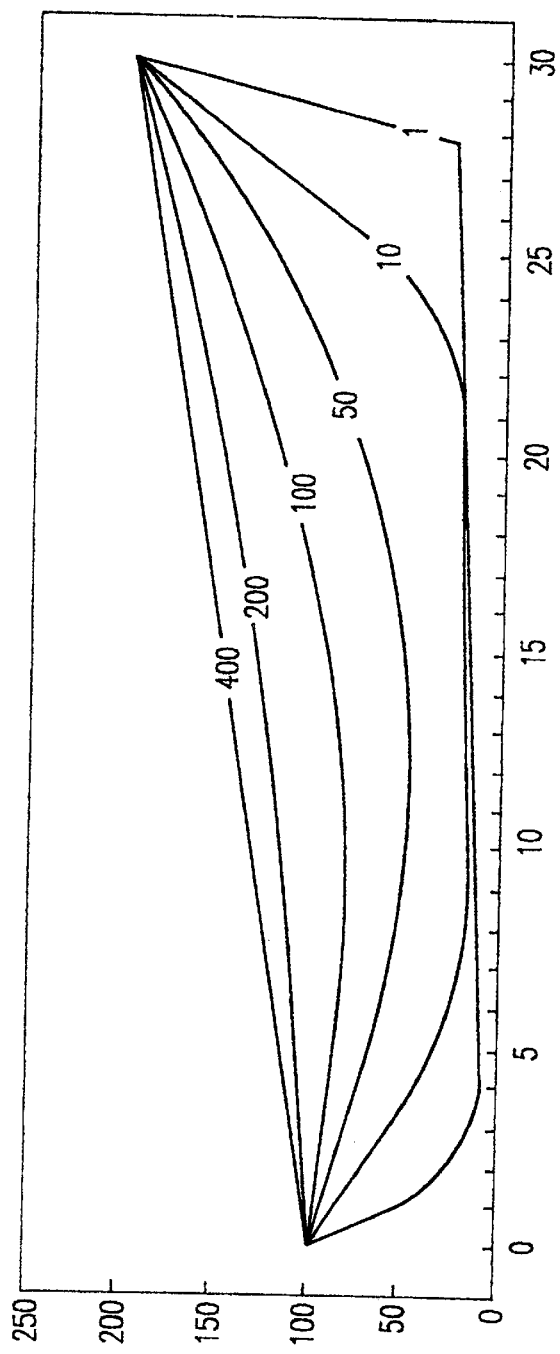
Figure 19:
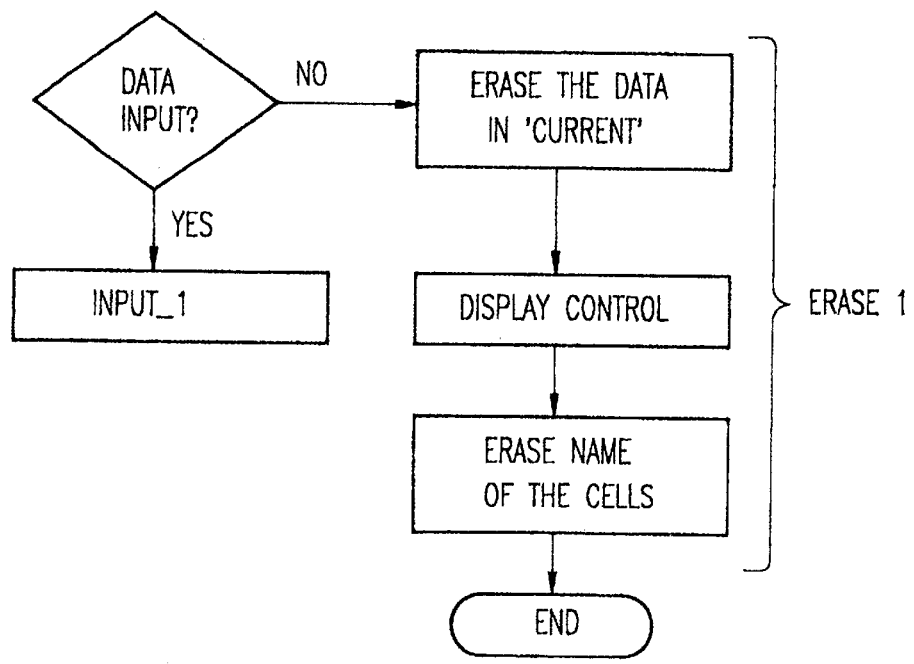
FIGS. 19, 20 and 21 are flowcharts of the subroutines ERASE_1, ERASE_3 and ERASE_4 used in the PDIC.

FIGS. 17 and 18 show how many recalculations would be needed to get a linear interpolation. When the interval between observed data is around 14 units, more than one hundred recalculations are needed (FIG. 17). When the interval between observed data is around 30 units, more than four hundred recalculations are needed (FIG. 18). After the recalculation of the HOKAN cells, program execution terminates.

Figure 21:
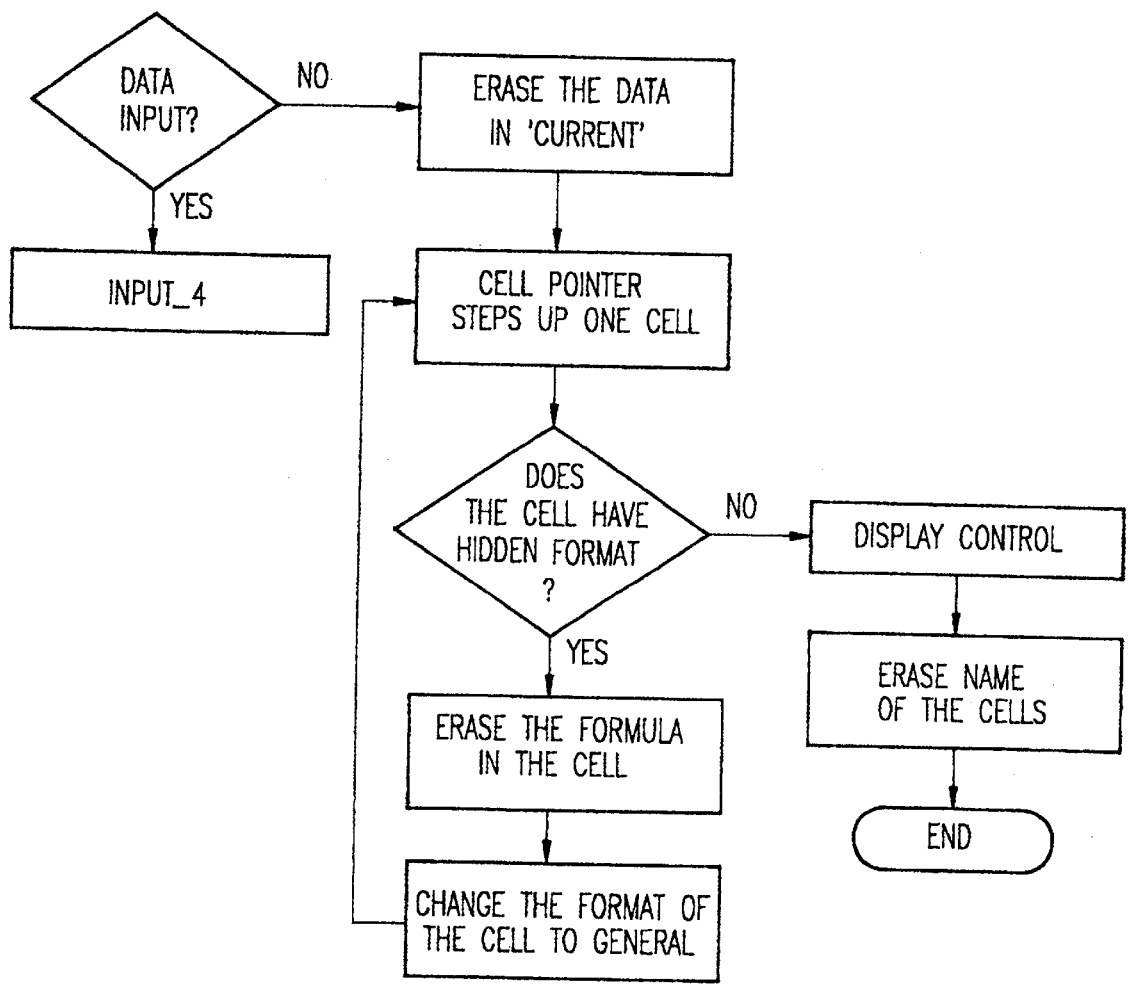

The program of the CMFCS executes the ERASE_4 subroutine if the user does not enter any data in the example of column 26 of FIG. 10. The ERASE_4 subroutine, illustrated in FIG. 21, functions in a manner similar to that of ERASE_2. First, the cell pointer at CURRENT moves up one cell. If the cell has a hidden format, the formula of the cell is erased, and the format of the empty cell is changed to general. This process is repeated, until the cell pointer encounters a cell with real data and a non-hidden format. The cell pointer then jumps to CURRENT. The name of the cell and the data in the cell are erased, and program execution terminates.

Figure 28:
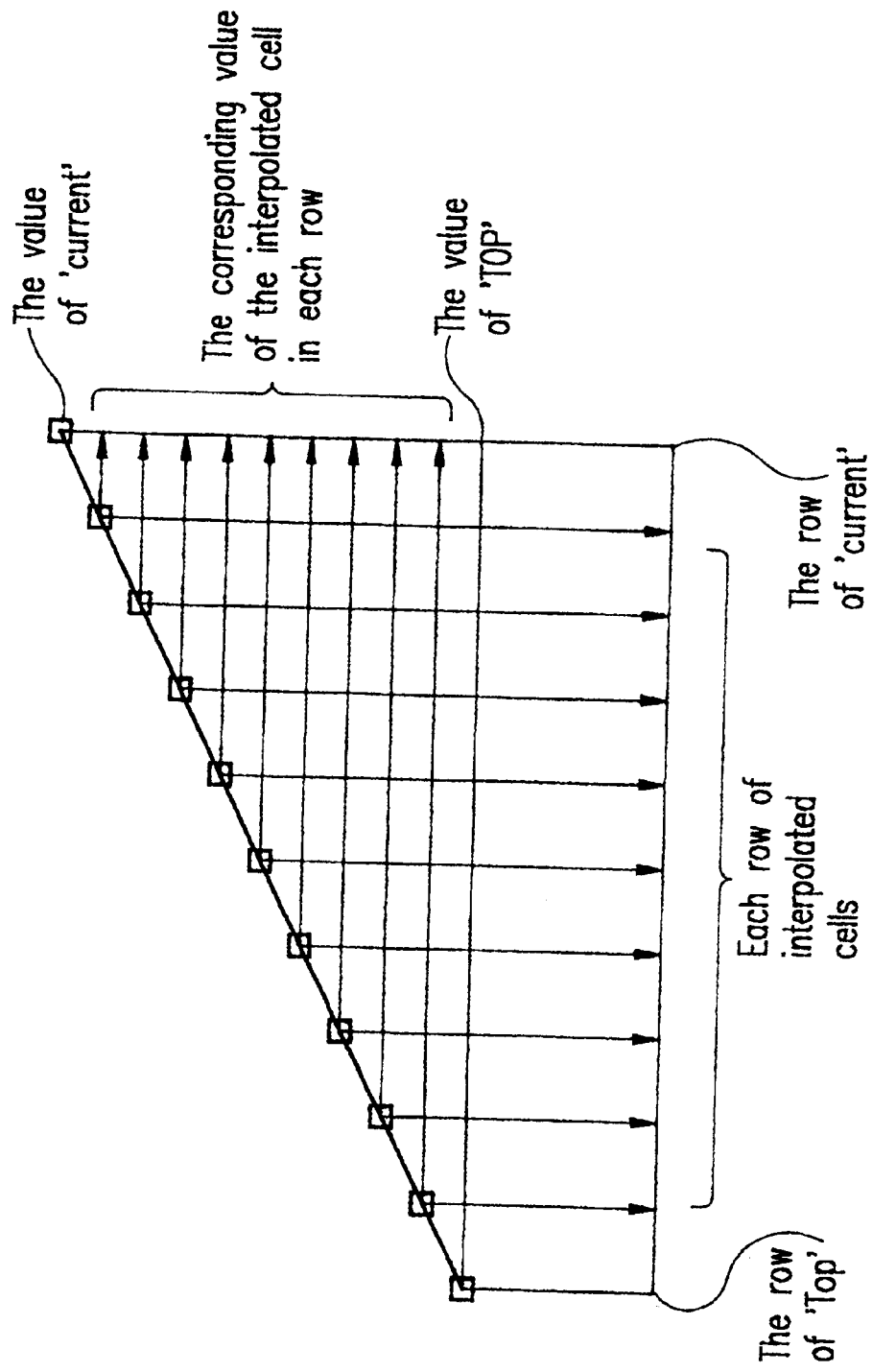
FIG. 28 graphically illustrates the gradient method of interpolation.

Instead of interpolating by repeated averaging as described above, the interpolation can use a built-in function of the Lotus program. This method is referred to as proportional allocation. In FIG. 28 the horizontal axis refers to the row numbers of the cells. The vertical axis represents the values of the cells. To interpolate between two items of real data, a gradient is multiplied by given variables and an intercept is added thereto. In FIG. 28, the intercept is the value of TOP, and the variable is the row number on the x axis. The gradient is arrived at by determining the difference between the value in the current and the value in the top cells, and dividing that difference by the number of rows between the current and the top cells. By substituting the row number for the variable, the corresponding value for each interpolated cell can be determined.

FIG. 29 illustrates an example of the proportional allocation method. The corresponding value of the interpolated cell of each row can be calculated directly by this method. The line chart obtained by this method is shown in FIG. 30.

Figure 9:
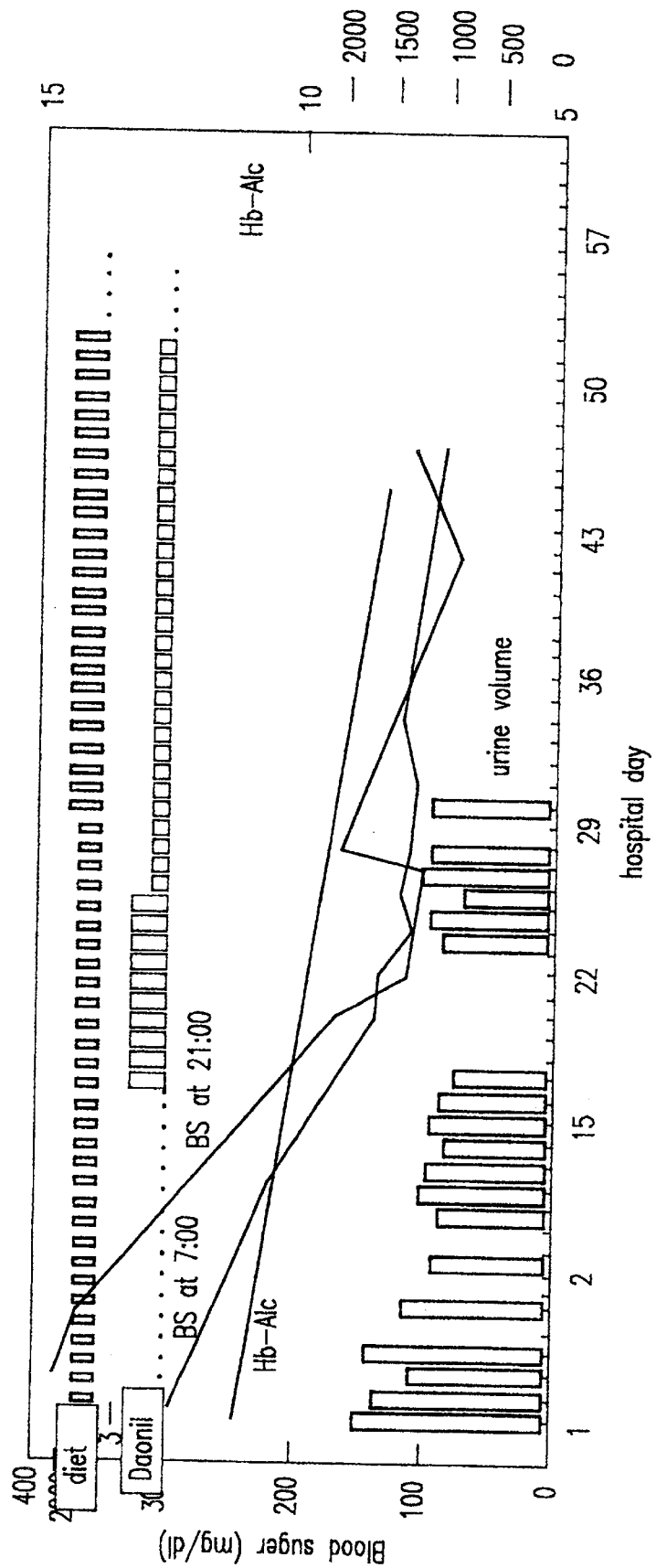
FIG. 9 illustrates a graphic medical chart using information shown in FIG. 7.

Graphical medical charts be designed so that therapeutic data as well as clinical data are simultaneously shown on the same chart with the same time scale so the user can comprehend changes in the clinical data and the influence of therapies. To create a graphical medical chart several charts are created, which are then overlapped and combined using the same time scale. In the chart, the X-axis is always time (e.g., hourly, daily, weekly, monthly, or annually). Some charts have a double Y-axis. The line chart is suitable for expressing the changes in the clinical data. Other charts are bar charts, which are especially suitable for indicating therapeutic methods on the medical chart. For example, FIG. 9 shows when the therapy starts, the amount of drugs administered, and how much of a special diet is prescribed. Bar charts are also used for some laboratory or other observed data. The background of the overlapping charts is transparent, and the margins are clear. The title and/or the legends are erased or changed in their position or size. Based on the same time scale, other graphic remarks or short explanations with transparent backgrounds and free margins can be added to the chart if it is required. Many predesigned templates for each clinical problem or diagnosis can be prepared. Doctors or other medical staff can select and modify the templates according to the specific needs in each patient case.

Figure 22:
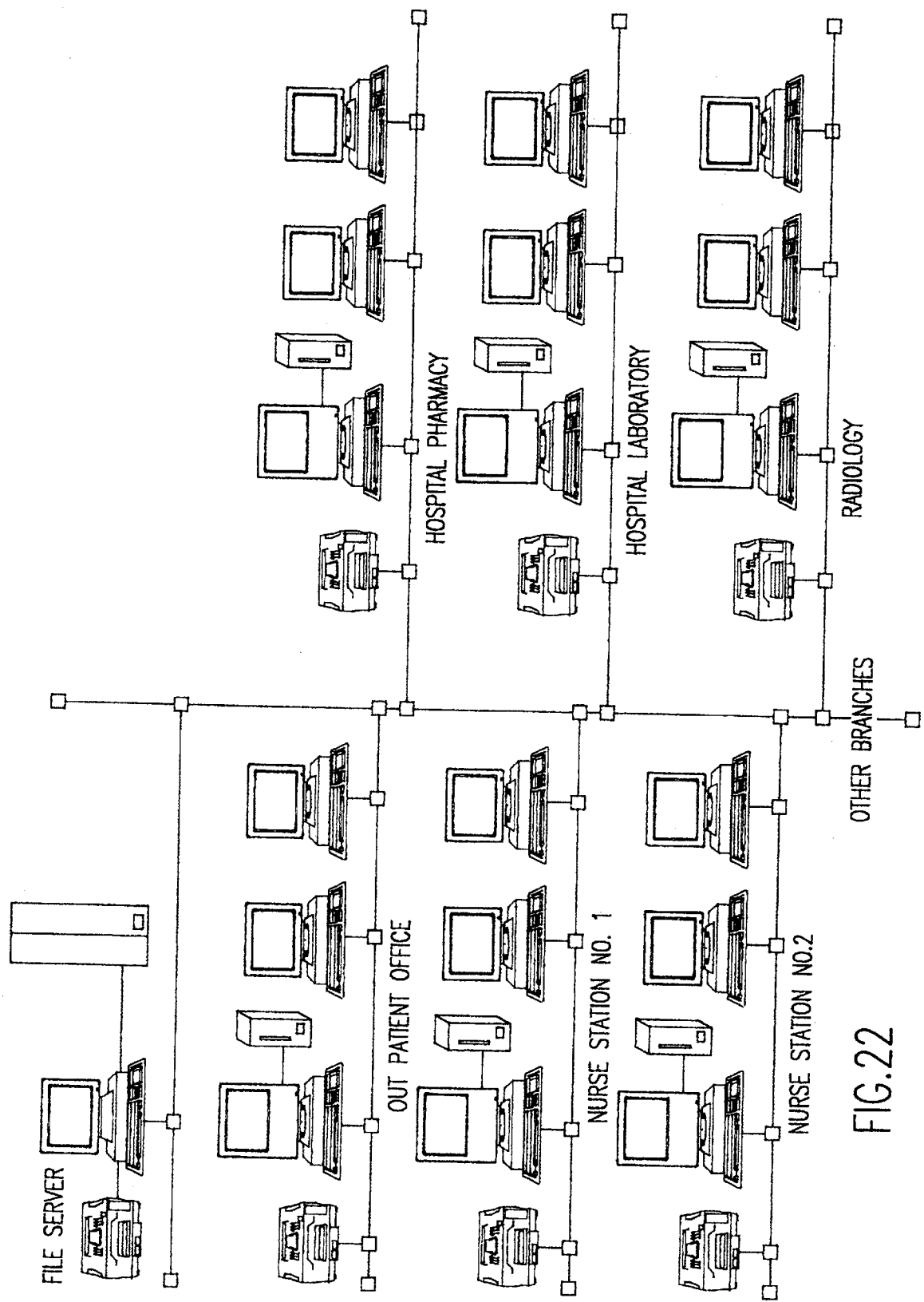
FIG. 22 illustrates a diagram of a client server system in which the DBMS with NTA operates, and in which the CMFCS can be applied more effectively.

By using a client server system as shown in FIG. 22, data stored in a server or other client database management system (DBMS) could be automatically selected and reconstructed in a flowsheet by the modified PDIC unit. In this situation, data from multiple entry sources is managed by the server DBMS. The CMFCS plays a role in data summation and presentation.

Figure 23:
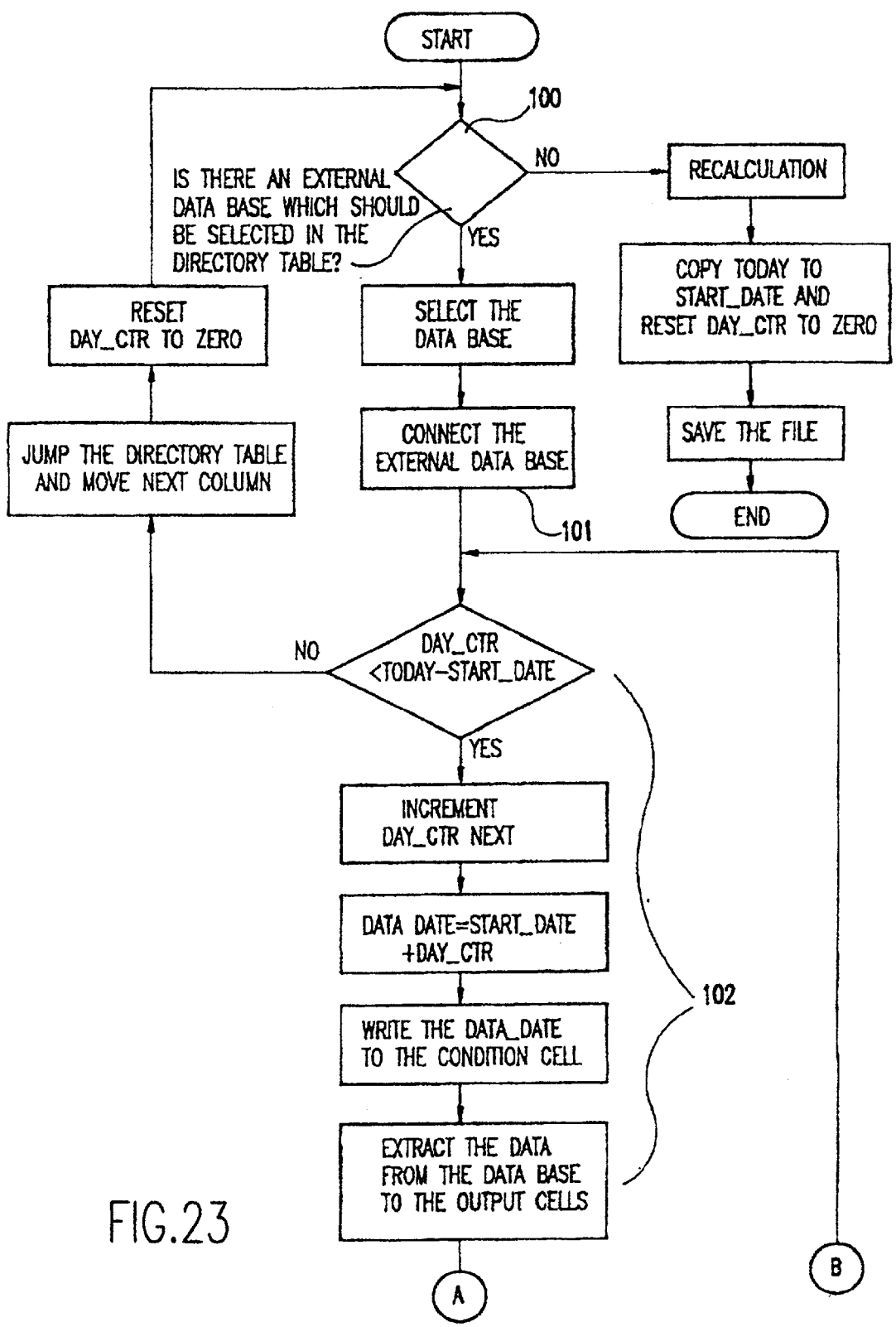
FIGS. 23 and 24 are flowcharts of a CMFCS program adjusted to a client server system.
Figure 24:
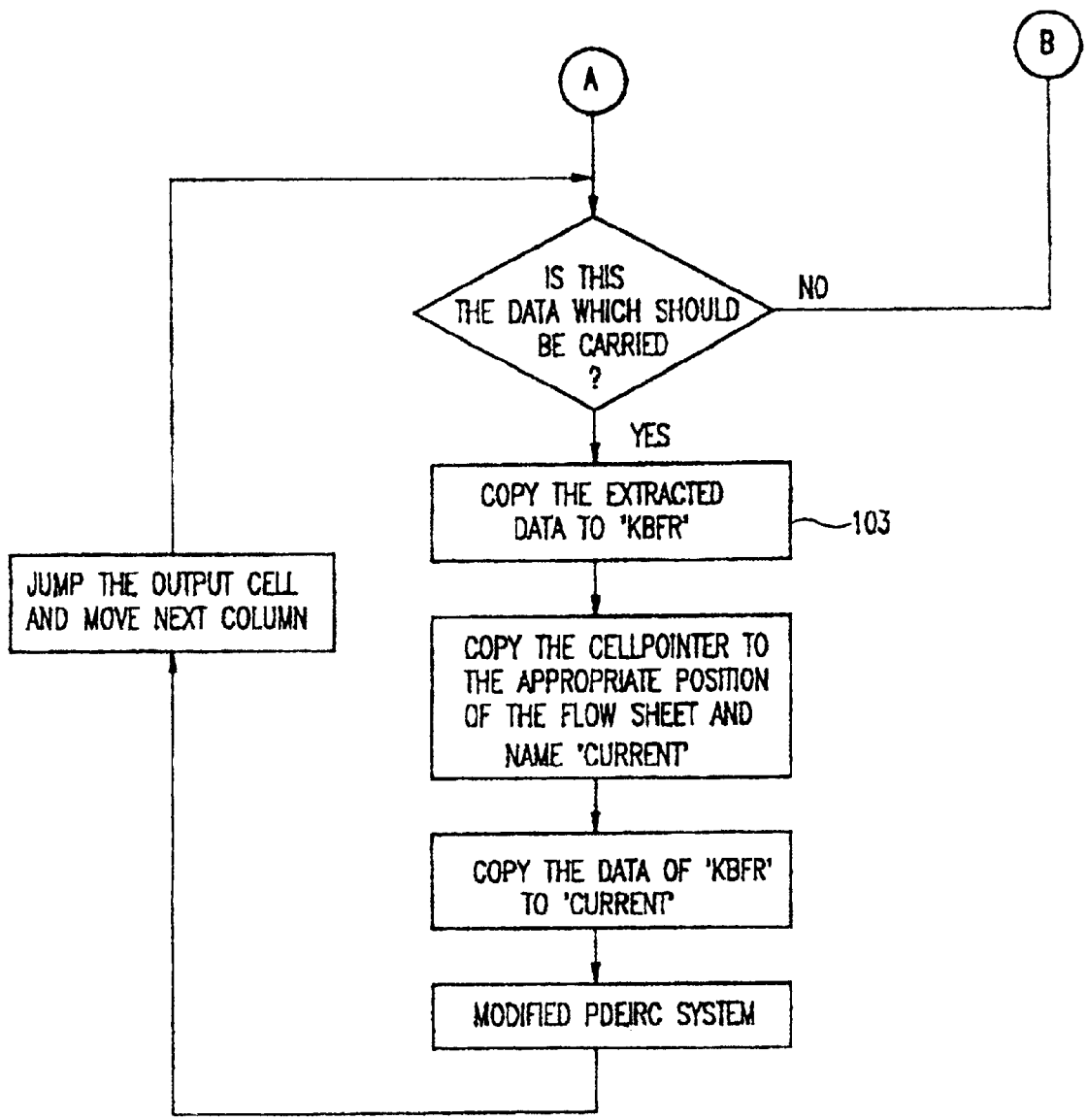

FIGS. 23 and 24 are flowcharts illustrating the program of the CMFCS for a client server system in which the POMR worksheet of the CMFCS is linked to external databases stored in other locations. For this purpose, it is necessary for the CONNECTION unit to be able to determine the name of the directory, the file name of the external databases, the name of the condition area, and the output area in the worksheet. The CONNECTION unit does this via the directory table. FIG. 53 is an example of a directory table. In FIG. 53, each column represents a separate external data base. The CONNECTION unit connects the worksheet to external databases in the sequential order of the columns in the directory table.

In this client and server system, the client personal computers as well as the server computers work in a nonstop operation. In the client personal computer in the nurse station, each patient's CMFCS file is automatically and serially opened, according to a time schedule. The macro program automatically connects to external databases, extracts data consistent with criteria from the databases, and reconstructs the data in the modified flow sheet of the POMR.

After the start of the CONNECTION unit, the cell pointer jumps to the directory table, and determines whether there is an external database by checking the first entry in column 1 of the table, i.e., (DIRECTORY). If none exists, the path identified by "NO" at decision block 100 in FIG. 23 is executed. If one exists, the cells of the directory, that is, the file_name, the condition and the output in the column of No. 1 are assigned temporary names. The contents of the names (i.e., the FILE_NAME, CONDITION and OUTPUT of column 1 in FIG. 53) are copied to appropriate positions in the subroutine CONNECT of the program. The worksheet is linked to the external database by the execution of this subroutine. (Block 101 in FIG. 23.)

The program of the CMFCS then enters the extraction loop (sequence 102). In this subroutine, the program refers to the date calculation table shown in FIG. 54. The extraction loop is executed until the DAY_CTR (the day counter) is equal to the subtraction of START_DATE from TODAY. Next the DAY_CTR is incremented by 1, and the DATA_DATE is calculated by START_DATE+DAY_CTR. The DATA_DATE is then written to the proper cell in the condition area. The patient's data for the date contained in DATA_DATE is extracted from the external database according to the data items in the output area, which are the same as the column titles of the modified flowsheet, and are located 10 rows above it. The program writes this extracted data to the output area of a flowsheet. (See FIG. 55.) The program continues by executing the subroutine CARRY, in which the cell pointer jumps to the first output area and scans along the item titles until it encounters any extracted data, and the extracted data is copied to KBFR (block 103 in FIG. 24). The cell pointer then moves down 9 rows which is the distance between the output area and the modified flowsheet, and then it moves down the number of rows equal to the difference between DATA_DATE and FIRST_DATE. The cell at the cell pointer is named CURRENT. (See FIG. 55) The program executes the modified PDIC unit (PDIC_2) which places the data in the proper location in the flowsheet.

There are only a few differences between the modified PDIC unit (i.e., the PDIC unit that reads an external database) and the ordinary PDIC unit. In the PERCEPTION subroutine, the first decision logic shown in FIG. 10 can be simpler, because the titles are not frozen. When the row of TOP is less than 151, and the row of BOTTOM is 8192, INPUT_4 is selected as the interpolation subroutine. The interpolation subroutines INPUT_4, INPUT_5 and INPUT 6 do not have the codes for the data entry dialog box from the keyboard, but the data stored in KBFR is directly written to CURRENT. The following interpolation and recalculation subroutines are the same as those of the ordinary PDIC unit except for the end of the program. The modified PDIC unit does not have the erase subroutine and the display control subroutine.

In the modified PDIC unit, the cell pointer returns to the cell in the output area, moves to the next column, and the program continues. The cell pointer reaches the end of the titles in the output area, then the program returns to the extraction loop to extract data on the next day from the external database. When the DAY_CTR reaches a point equal to the subtraction of the START_DATE from TODAY, the cell pointer goes back to the directory table to link the worksheet to the next external database identified in the next column of the DIRECTORY row, and the DAY_CTR is reset to zero. When there is no external database which could be selected in the directory table, the date of TODAY is written as the START_DATE, and the DAY_CTR is reset to zero. The recalculation subroutine is executed, the worksheet is saved, and the program terminates.

The CMFCS applies to medical studies or drug trials. In order to illustrate the usefulness of the CMFCS for medical studies, an actual study is described in relation to FIG. 56.

FIG. 56 is a part of collected information on serum creatine phosphokinase (CPK) levels in patients with polymyositis and dermatomyositis observed during a certain period of time in the hospital. The rows refer to hospital days, and the columns identify patients' names or patients' identification numbers. The data of a single patient's column is collected at irregular intervals. The data of combined columns in the cases of many patients are more random.

Figure 25:
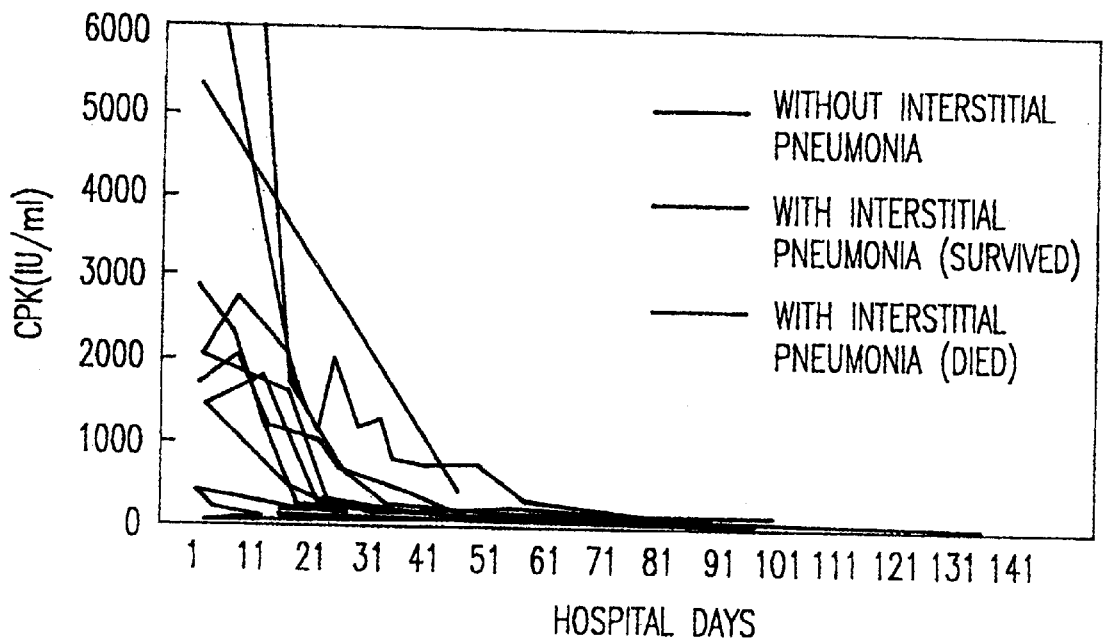
FIGS. 25 and 26 are respectively graphic line charts of CPK and lactate dehydrogenase (LDH) in the myositis patients.
Figure 26:
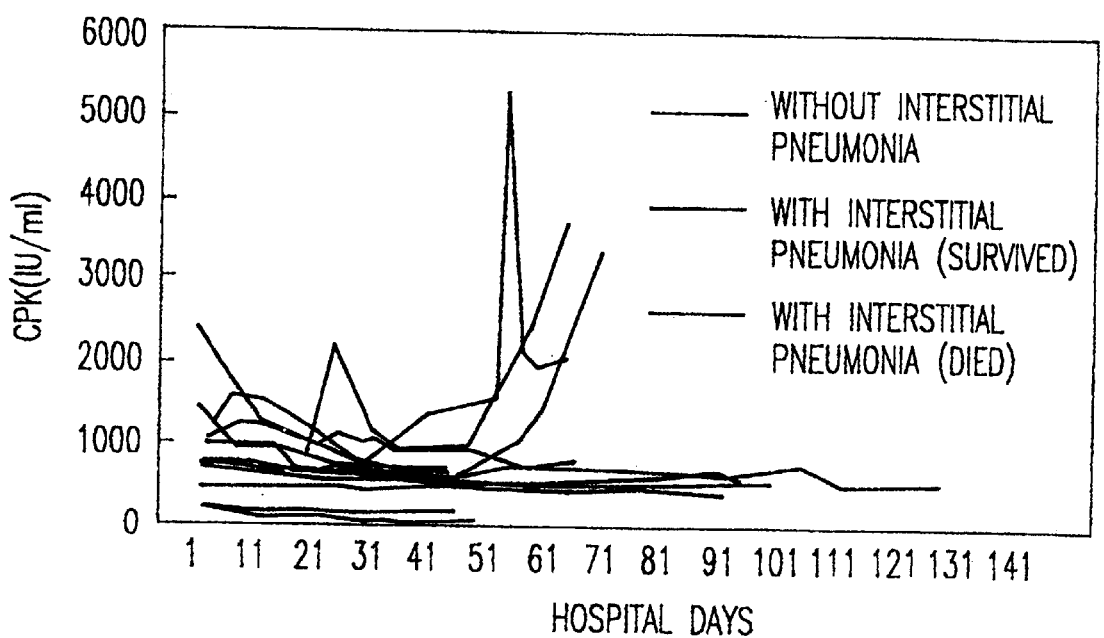

Based on these tables of the CMFCS, line charts of CPK and lactate dehydrogenase (LDH) in the myositis patients are made as shown in FIGS. 25 and 26 respectively. It is possible to collect and compare many patients' data of CPK and LDH observed at irregular intervals by using the CMFCS, because it has a standardized time scale and virtual data is interpolated by an appropriate formula.

In this study, 15 patients with polymyositis or dermatomyositis were classified into three groups; patients without interstitial pneumonia (IP) who survived, 5 patients with IP who survived, and 4 patients with IP who died. Serum CPK levels decreased after hospital admission in all three groups. This finding suggests that steroid therapy after admission was very effective for myositis in these patients. Three out of 4 patients with IP who died had very low levels of CPK at the time of hospital admission. In other words, the patients showed skin manifestations with minimal myositis.

Serum LDH levels also declined in most patients after admission. In 3 out of 4 patients with IP who did not survive, however, LDH levels rose in spite of intensive steroid or immunosuppressive treatment over the length of their hospital stay. Discrepancy between serum CPK and LDH levels suggested grave prognosis in the patients with myositis in this study.

Figure 27:
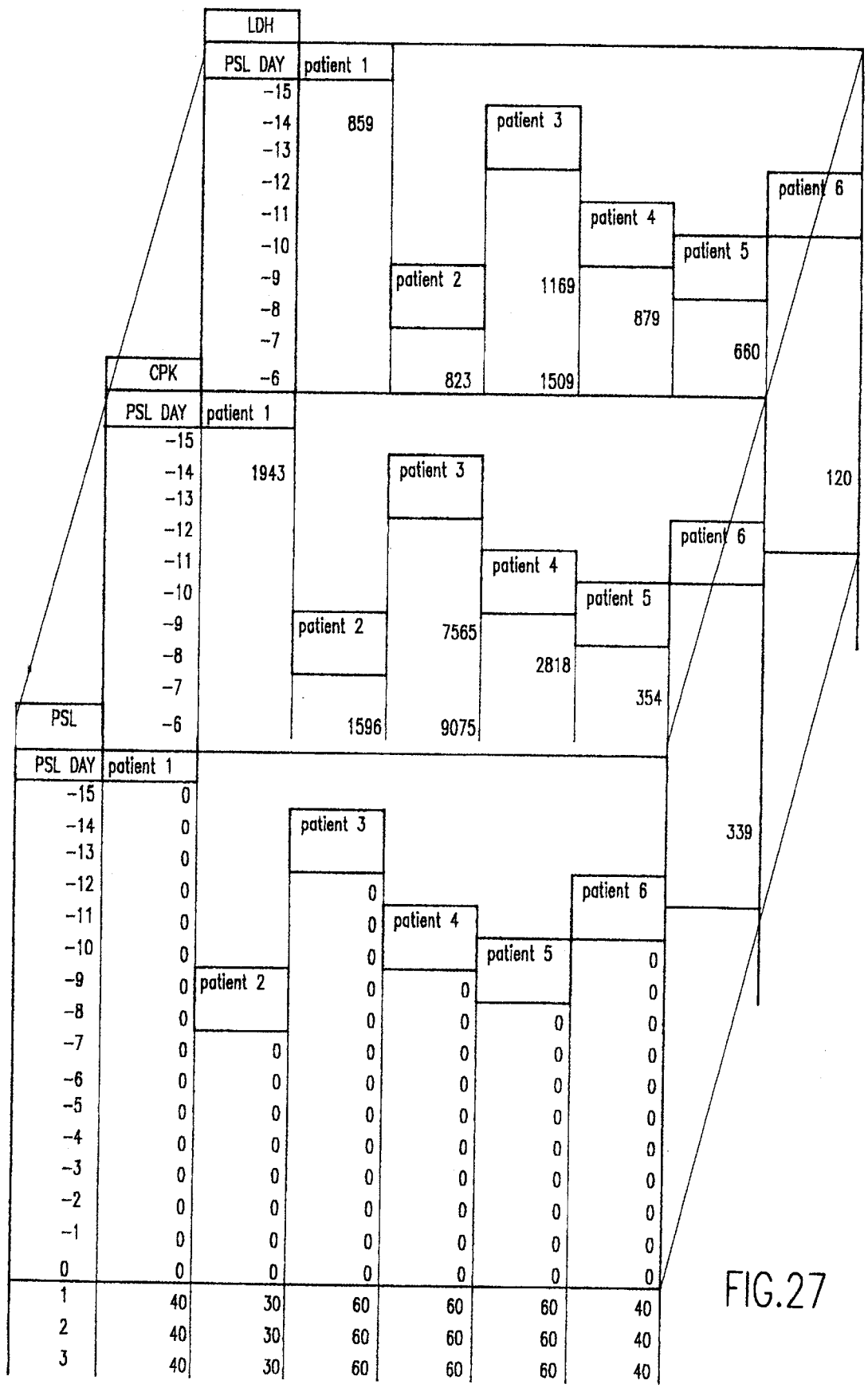
FIG. 27 is a conceptual drawing of multi-layer worksheets adjusted to the starting date of each patient's steroid administration.

Newer spread sheet programs have a function of multi-layer worksheets. This makes it possible to perform more specific analysis of the clinical effects of therapeutic factors such as the administration of drugs. FIG. 27 is a conceptual drawing of a multi-layer worksheet adjusted to the starting date of each patient's steroid treatment. This method can show more clearly the specific effects of steroid therapy on myositis patients.

Database Management System With Nested Time Axis

FIG. 22 illustrates a computer system upon which the Database Management System with Nested Time Axis (DBMS With NTA) may operate. The system consists of a file server 41, and multiple stations 42 which can access the database files in the file server 41. The file server 41 executes the DBMS with NTA, and the stations 42 run the CMFCS which receives data from the server 41 and constructs modified flowsheets of POMR. The file servers 41 work in a nonstop operation and each table of the DBMS with NTA is automatically opened according to a preset time schedule. Although this system executes in Lotus 1-2-3 for Windows version 4.01, and the programs are written in the 'macro' language of Lotus 1-2-3 for DOS, one of ordinary skill in the art could easily translate it to newer and more powerful relational database programs such as Oracle, Sybase, Infomix, MS SQL server or others.

Figure 31:
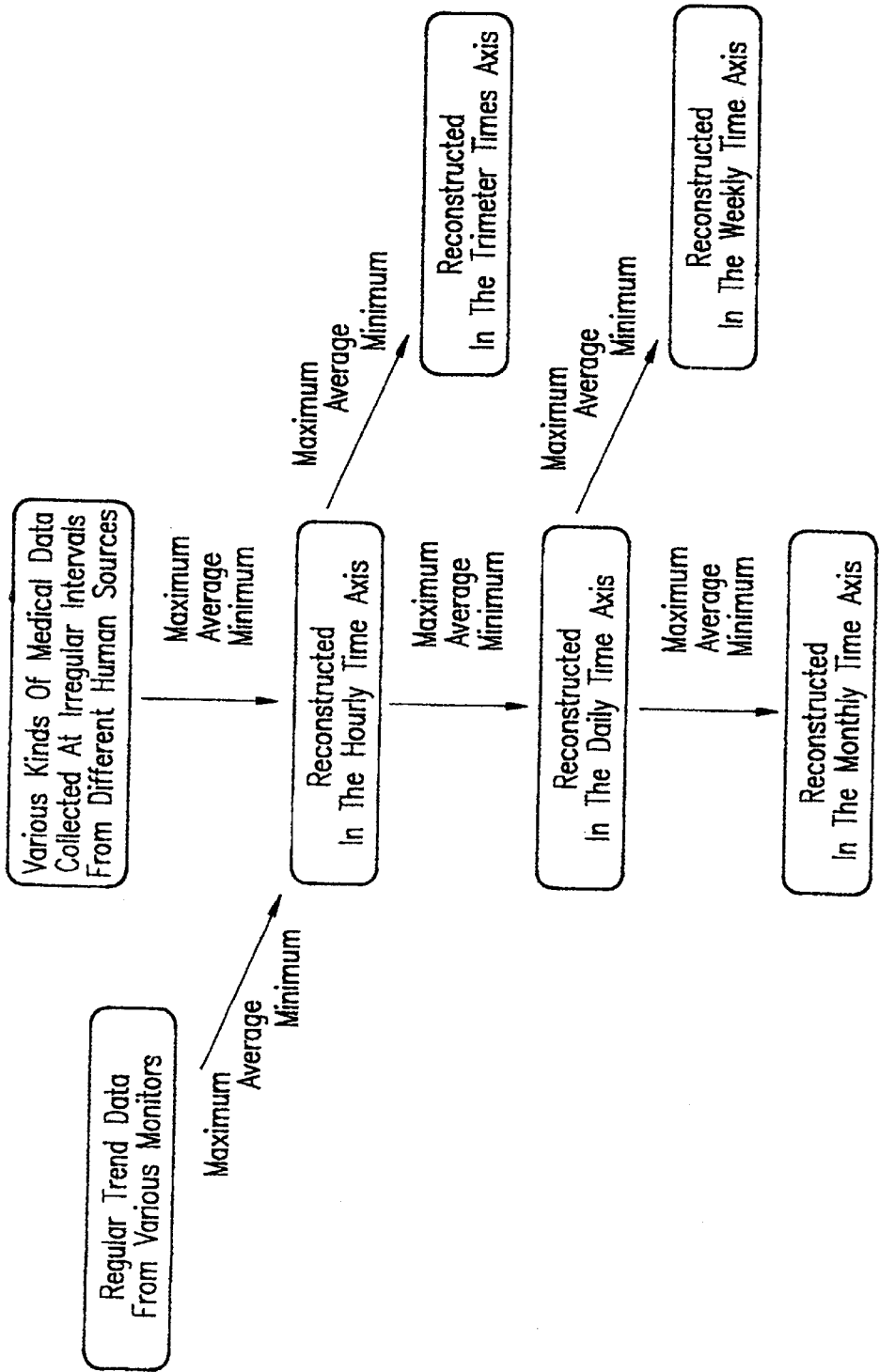
FIG. 31 illustrates the data processing flow in the DBMS with NTA.

FIG. 31 illustrates the data processing flow in the DBMS with NTA, although other combinations of the root and progeny database tables are possible. Most medical data is collected at irregular intervals from different human or machine sources, and is stored as a record in databases in the server computers. Some data regularly comes from various kinds of monitoring machines and directly enters the processing unit and memory of file server 11. Records of the database table are extracted at hourly intervals, and the average, maximum and minimum valves for the data in those records are calculated. A progeny database table is reconstructed with an hourly time axis by the DBMS with NTA. Then the reconstructed database with the hourly time axis serves as the root database for progeny database tables in the trisection or daily time axis. The database with the daily time axis plays the role of the root database for the progeny database tables in the weekly or monthly time axis.

Figure 33:
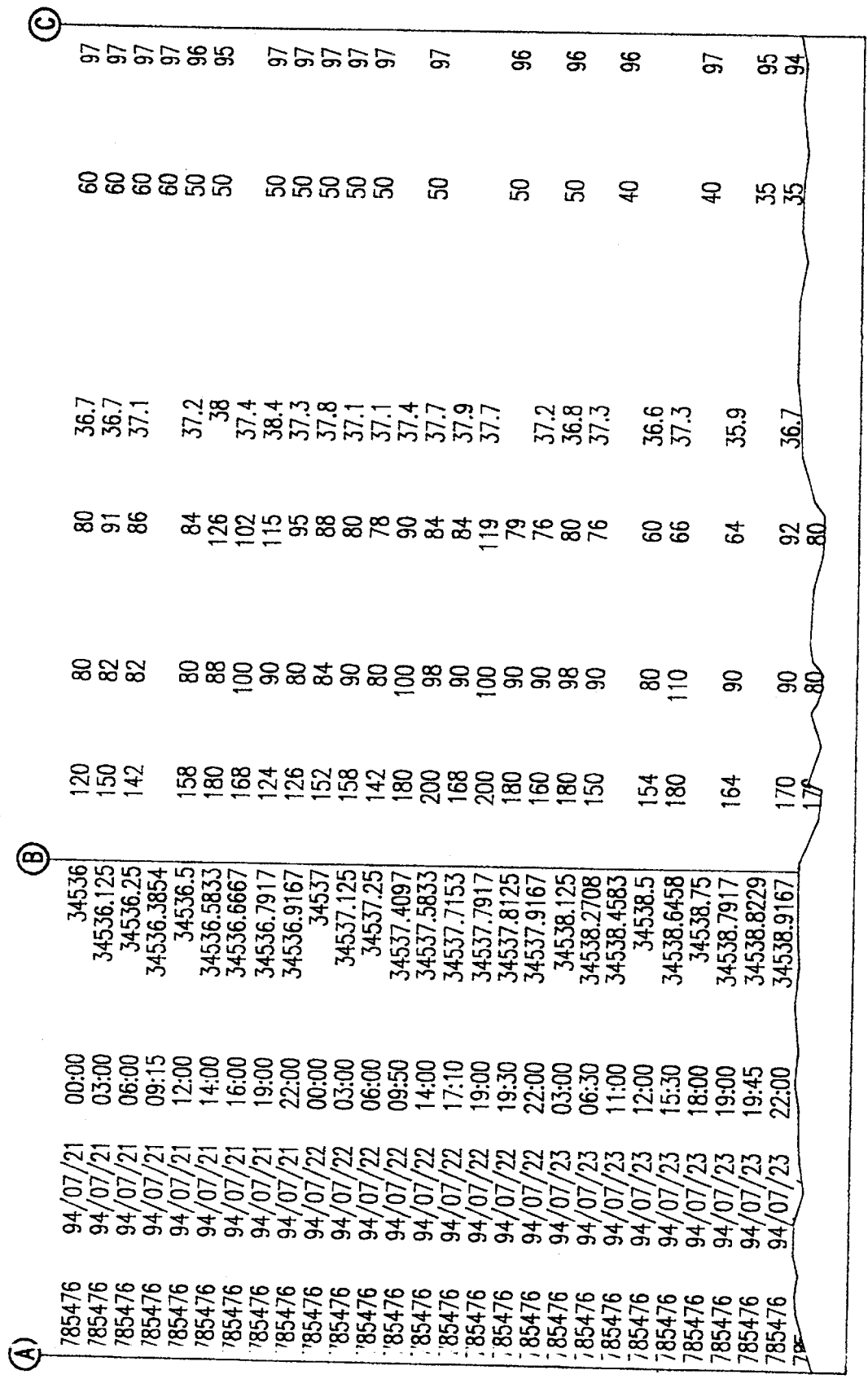
Figure 34:
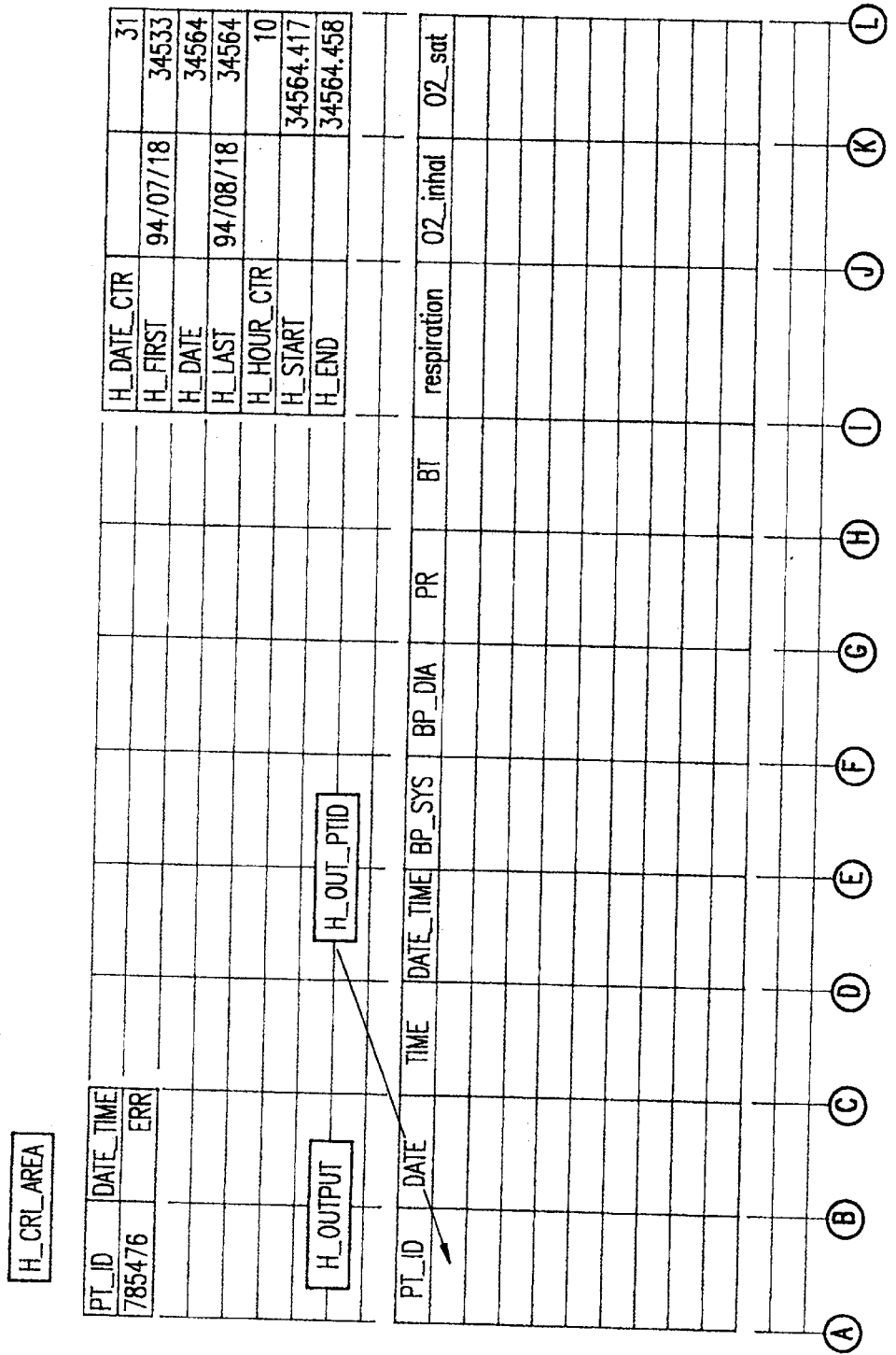
Figure 35:
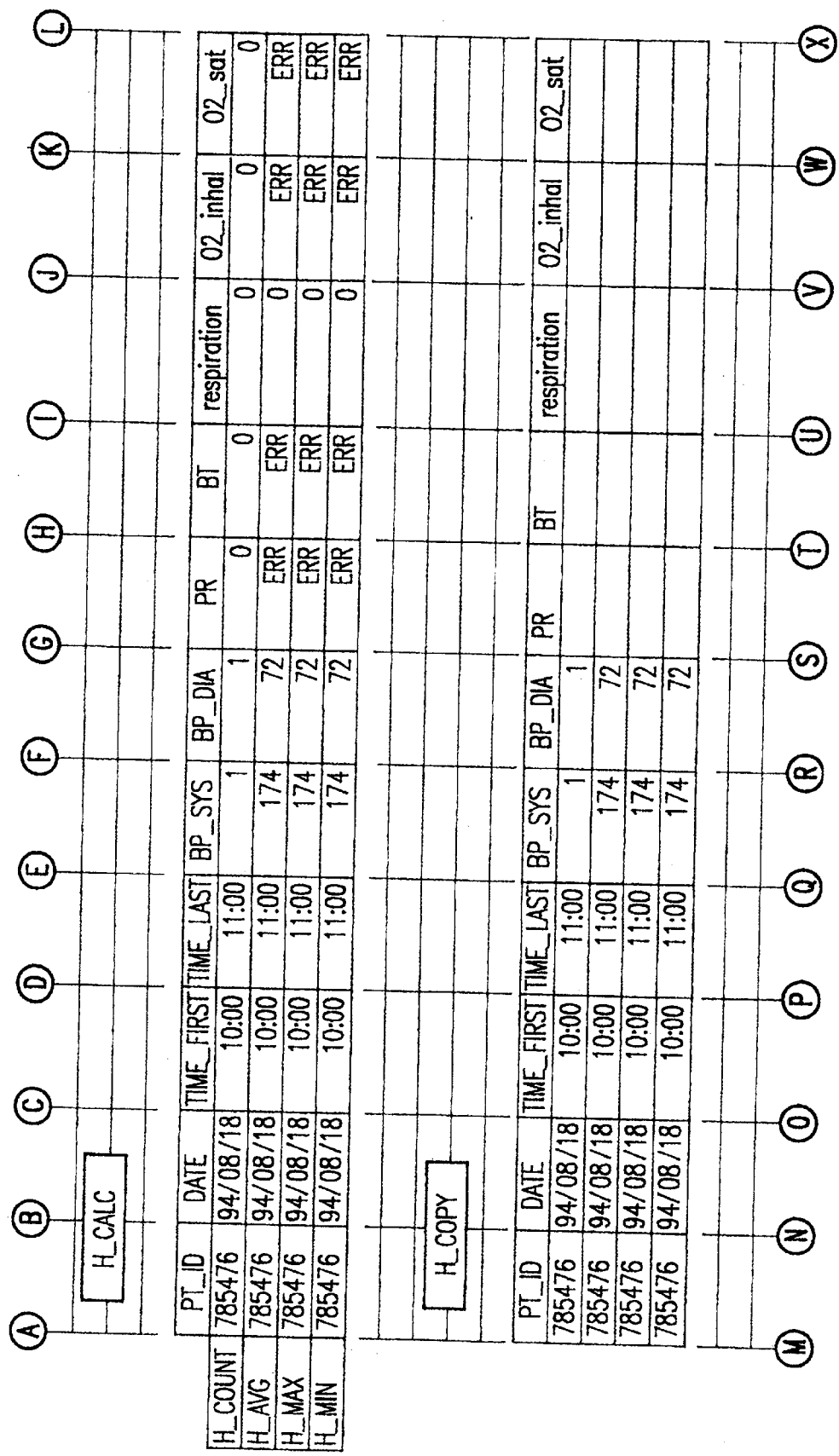

The database of ORIGINAL_DATA illustrated in FIGS. 32 and 33 consist of the fields of patient identification, the date and the time when the data is collected, and the data items. Nurses enter patient IDs, date and time, and observed data in each field into the computer, which automatically calculates the date plus the time in the DATE_TIME field. In this example, each record contains a patient's systolic blood pressure, diastolic blood pressure, pulse rate, body temperature, mode of respiration, $O_2$ administration and saturation of arterial $O_2$ at irregular intervals.

Figure 47:
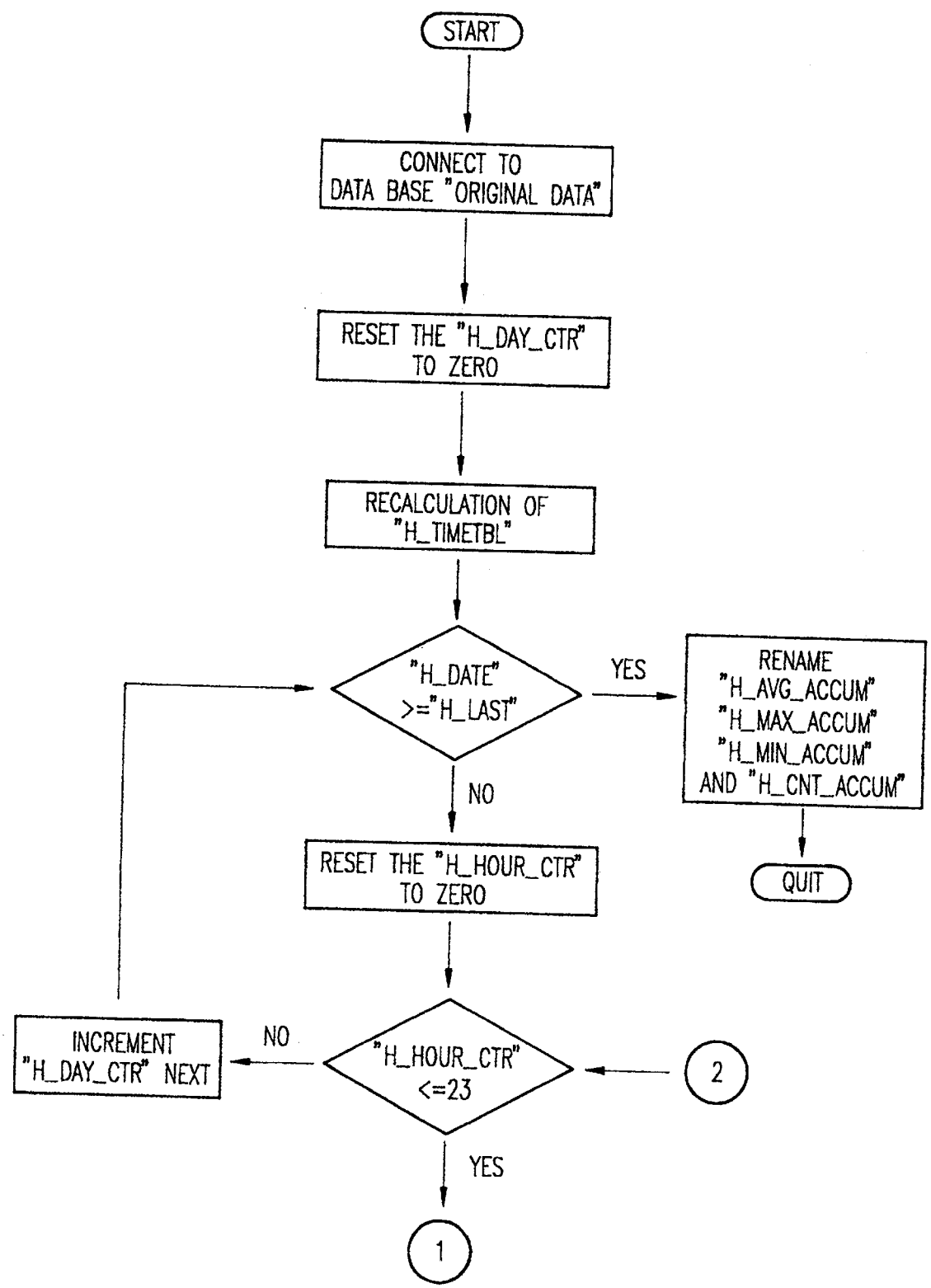
FIGS. 47 and 48 are flowcharts of the process which creates the HOUR level in the DBMS with NTA.
Figure 48:
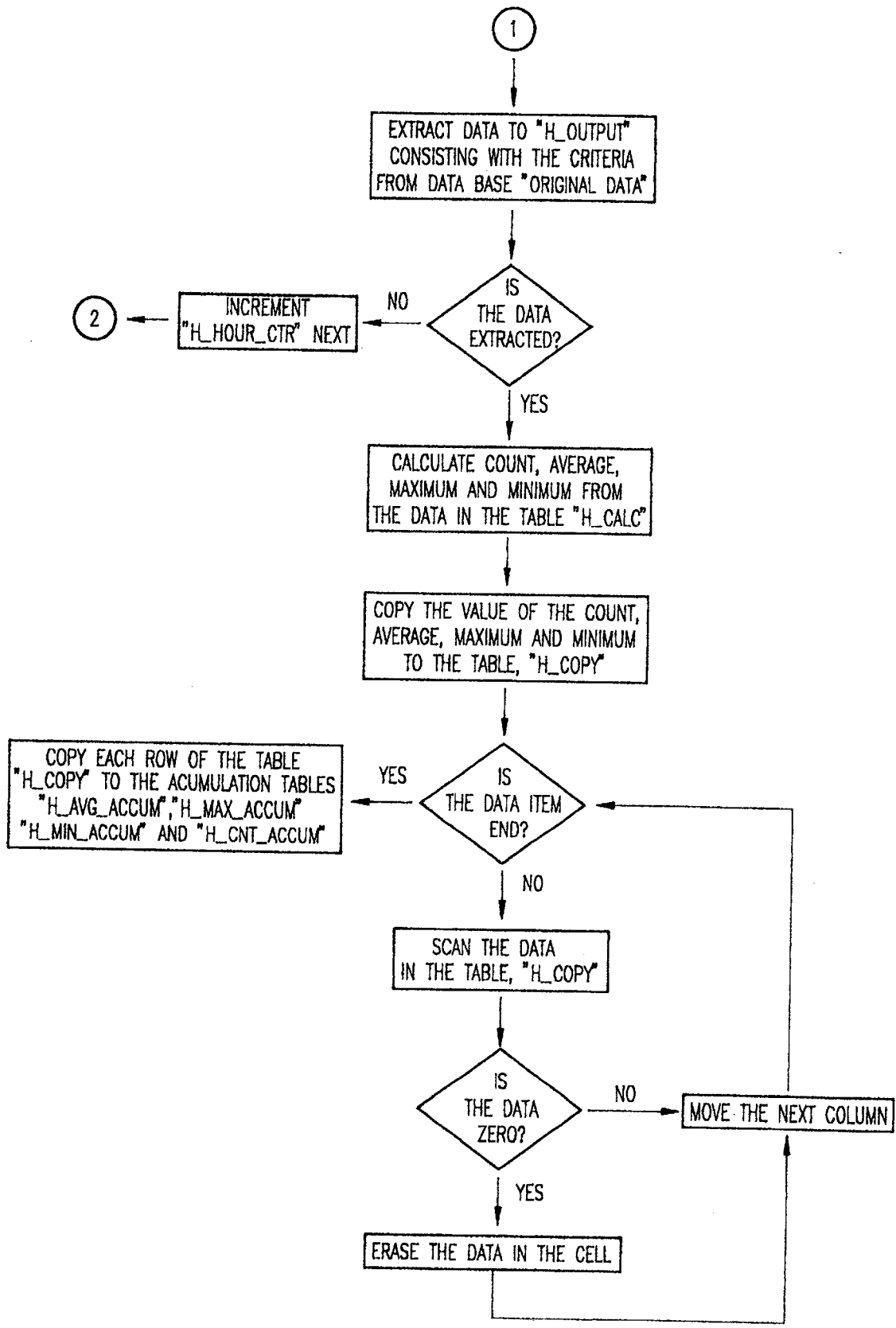

The HOUR level program in the DBMS with NTA extracts a patient's records within a single hour interval into a worksheet (named "vital_hour") (FIGS. 47, 48). For the extraction, the program uses several data areas—H_TIMETBL, H_CRI_AREA, H_OUTPUT, H_CALC, and H_COPY in the worksheet (FIGS. 34, 35 and 36, FIGS. 37 and 38).

The time table H_TIMETBL contains day and hour counters—H_DAY_CTR and H_HOUR_CTR. The H_DAY_CTR is incremented after each cycle of extraction on a particular day. The date the program starts and the date the program stops are input into cells at the addresses M2 and M4 of the spread sheet respectively. The cells H_FIRST and H_LAST have the functions @ROUND(M2,0) and @ROUND(M4,0) which return the rounded values of the start and stop dates of the program respectively. The cell H_DATE calculates the date for the extraction by the formula +H_FIRST+H_DAY_CTR. The H_HOUR_CTR keeps track of the hour of the extraction which starts at 0:00 and ends at 23:00. While the cell H_START computes the hour when the extraction starts by the formula +H_DATE+(H_HOUR_CTR)/24, the cell H_END calculates the hour when the extraction ends by the formula +H_DATE+(H HOUR_CTR+1)/24.

When the program starts, the database table ORIGINAL_DATA ("vital_org") serves as the input. The criteria for the extraction, i.e. the patient's ID and the formula of H_CRI_AREA (FIGS. 37 and 38), which determines if a record falls within a time period, are written in H_CRI_AREA in the worksheet, "vital_hour". One of the criteria, the patient's identification, is already copied. The other criterion is that the field DATE_TIME should contain a value which is greater than H_START and less than or equal to H_END. After these definitions are finished, H DAY_CTR and H_HOUR_CTR are reset zero, and H_TIMETBL is recalculated in order to increment H_START and H_END to the next hourly interval for which data will be extracted.

The records which meet the criteria are extracted from ORIGINAL_DATA and placed into the table H_OUTPUT (FIGS. 34, 35 and 36) for each extraction cycle (i.e. hourly, daily, etc.). If more than one record is extracted for a particular time period, a count, an average, and a maximum and minimum are calculated and placed into in the table H_CALC. If a single record is extracted, the average, maximum and minimum are the same. In the case where no record is extracted, the subsequent steps in the extraction cycle are skipped, and the H HOUR_CTR is incremented. The values stored in H_CALC, i.e. the count, average, maximum and minimum of each field of the extracted records, as well as the patient's ID, the date and hour of the extraction are copied to the table H_COPY. The cell pointer then scans each value of H_COUNT in H_CALC. If the value is zero, the rest of the cells in the column are cleared. Zero values in H_COUNT cause Lotus 1-2-3 to report ERR values in the remainder of the column. Each row of the table H_COPY is named H_COUNT, H_AVG, H_MAX and H_MIN, and are delivered and appended to the accumulation tables named H_CNT_ACCUM, H_AVG_ACCUM, H_MAX_ACCUM, and H_MIN_ACCUM. The H_HOUR_CTR is then incremented. If H_HOUR_CTR is less than or equal to 23, the extraction cycle is reiterated. If H_HOUR_CTR is more than 23, the H_DAY_CTR is incremented, and H_DATE is updated.

If H_DATE is less than H_LAST, H_HOUR_CTR is reset to zero, and the extraction is reiterated. If H_DATE is greater than or equal to H_LAST, the accumulation tables H_AVG_ACCUM, H_MAX_ACCUM, H_MIN_ACCUM and H_CNT_ACCUM are redefined and renamed, (so that a subsequent running of the program will not destroy the data therein), and program execution terminates.

The program of the TRISECTION level in the DBMS with NTA extracts the patient's records three times per day—in the morning, evening and night (FIGS. 39 and 40). The manner of execution is very similar to the HOUR level. Whereas the root database table for the hourly extraction is the original database (FIGS. 32 and 33), the database table which acts as the root for the TRISECTION portion is H_AVG_ACCUM. T_START and T_END, which define the time period within which a record must fall in order to be extracted during this cycle, contain the formulae +T_DATE+(T_HOUR_CTR)/3 and +H_DATE+(H_HOUR_CTR+1)/3 respectively. The formulae divide the day into three time periods—0:00–8:00, 8:00–16:00, and 16:00–23:00. When T_HOUR_CTR is greater than 3, T_DATE_CTR is incremented. The selection field of the input area and the criteria area are TIME_START, which should be greater than T_START and less than or equal to T_END.

The program of the DAY level is simpler than that of the HOUR or TRISECTION level (FIGS. 41 and 42). The database table which acts as input is H_AVG_ACCUM. The hour counter is not necessary for the DAY level, and the program has only the day counter—D_DAY_CTR. The date the program starts and the date the program terminates are input into the cells at the addresses M2 and M3 respectively. The cells D_FIRST and D_LAST have the functions @ROUND(M2,0) and @ROUND(M3,0) which return values for D_FIRST and D_LAST respectively. The cell D_FINAL calculates the daily interval from the first day to the last day, and adds plus one to the value. The cell contains the formula, @DATEDIF(+D_FIRST, +D_LAST, "d")+1. The cells D_START and D_END have the formulae +D_FIRST+D_DAY_CTR and +D_START+1 respectively. The selection field of the input area and the criteria area are TIME_START, which should be greater than D_START and less than or equal to D_END. In each daily cycle, the records in a single day are extracted. If D_DAY_CTR exceeds D_FINAL, the day accumulation tables are redefined and renamed, and program execution terminates.

The program of the WEEK level has a more complicated time table W_TIMETBL (FIGS. 43 and 44). The database table which is connected as the input area is D_AVG_

ACCUM. The date the program starts and the date it terminates are input into the cells at the addresses M2 and M3 respectively. The cells W_FIRST and W_LAST have the functions @ROUND(M2,0) and @ROUND(M3,0) which return values for W_FIRST and W_LAST respectively. The cell W_FINAL calculates the weekly interval from the first day to the last day, and adds plus one to the value. The cell contains the formula @TRUNC(@DAYS(+D_FIRST,+D_LAST, 1)/7)+1. The cell W_START has a formula to compute the date of Sunday when each extraction cycle starts. The formula is +W_FIRST-@VLOOKUP(@MOD(+W_FIRST,7),W_MOD,1)+W_CTR*7. The cell named W_END has a formula @W_START+6. The selection field of the input area and the criteria area is DATE, which should be more greater than W_START and less than or equal to W_END. If W_WEEK_CTR exceeds W_FINAL, the week accumulation tables are renamed, and program execution terminates.

In the program of the MONTH level, the database table which is connected as the input area is D_AVG_ACCUM (FIGS. 45 and 46). The date the program starts and the date it terminates are input into the cells at the addresses M2 and M3 respectively. The cells M_FIRST and M_LAST has the functions @ROUND(M2,0) and @ROUND(M3,0) which return values for M_FIRST and M_LAST respectively. The cell M_FINAL calculates the monthly interval from the first day to the last day, and adds one to the value. The cell contains the formula, @TRUNC(@DATEDIF(+M_FIRST, +M_LAST, "m"))+1. The cells M_START and M_END have the formulae @MONTH(+M_FIRST)+M_MONTH_CTR and M_START+1 respectively. In each monthly cycle, the records in a single month are extracted. The selection field of the input area and the criteria area is MONTH, which should be greater than or equal to M_START and less than M_LAST. If M_MONTH_CTR exceeds M_FINAL, the month accumulation tables are renamed, and program execution terminates.

From ORIGINAL_DATA, the program of the DBMS with NTA generates the 20 database tables with standardized time axes—H_AVG_ACCUM, H_MAX_ACCUM, H_MIN_ACCUM, H_CNT_ACCUM, T_AVG_ACCUM, T_MAX_ACCUM, T_MIN_ACCUM, T_CNT_ACCUM, D_AVG_ACCUM, D_MAX_ACCUM, D_MIN_ACCUM, D_CNT_ACCUM, W_AVG_ACCUM, W_MAX_ACCUM, W_MIN_ACCUM, W_CNT_ACCUM, M_AVG_ACCUM, M_MAX ACCUM, M_MIN_ACCUM and M_CNT_ACCUM.

Figure 50:
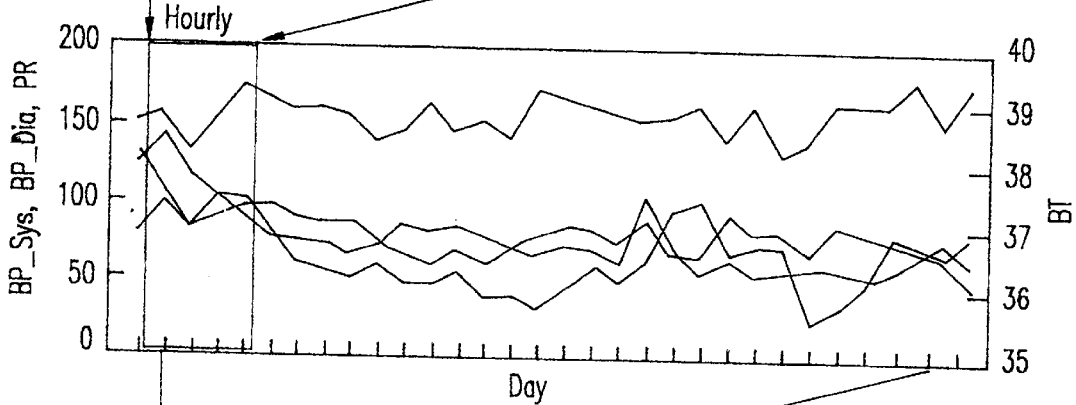
Figure 51:
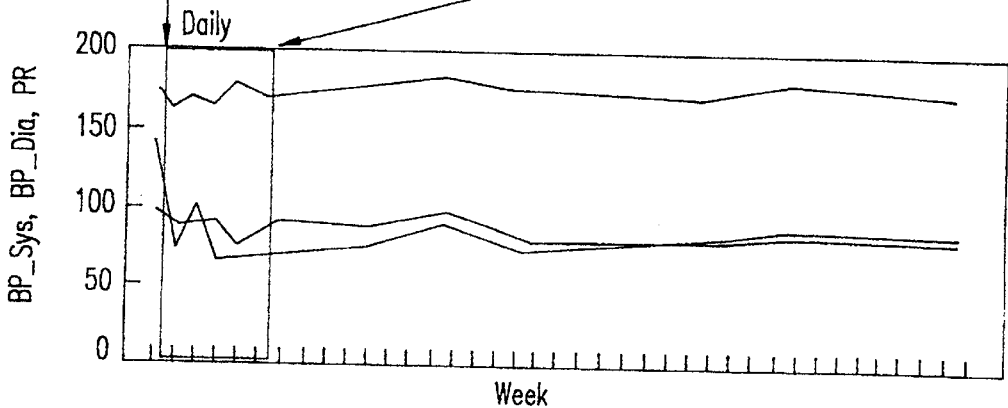

Proper database tables are chosen and connected to the corresponding CMFCS flowsheets with the same time axis. The CMFCS connected to the DBMS with NTA presents multiple charts of medical information with nested time axes. This method can show changes of clinical data from a short range view (the microscopic view), to standard range view, to long range view (the wide angle view) serially using several different time axes (FIGS. 49–51).

In the example presented in this document, the patient was a 63 year old male who had acute pneumonia with congestive heart failure. He also had diabetes mellitus and left hemiparesis after a stroke several years before. After emergency admission on Jul. 18, 1994, digitalis, theophylline and antibiotics were administered. The next day he complained of palpitation and chest discomfort. An attack of atrial fibrillation with severe tachycardia occurred. An intratracheal tube and a respirator were set, and defibrillation by electric defibrillator were given with verapamil and corticosteroid. The top figure (FIG. 49) with the hourly time axis shows several tachycardial attacks in the period between July 18 and 22. After blood pressure transiently fell down in the intubation, the circulatory dynamics gradually stabilized. On July 25, the respirator stopped and the intratracheal tube was taken away.

Figure 49:
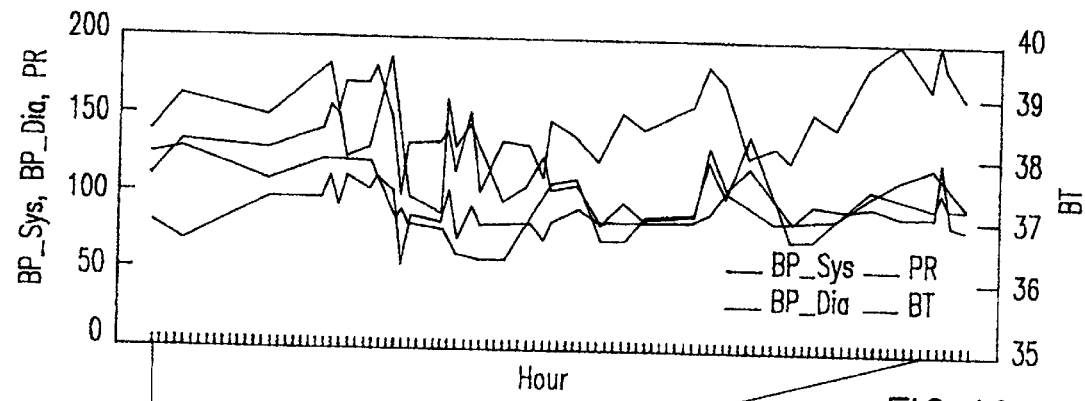
FIGS. 49 through 51 illustrate the computer displayed medical charts with hourly, daily or weekly time axis made by the DBMS with NTA and the CMFCS.

The middle figure (FIG. 50) with daily time axis summarizes FIG. 49 for the first four days. After the stormy episode in the first several days, the clinical course of the patient was stable. Until the middle of August, the patient could stand and walk. He was discharged on August 18. The bottom figure (FIG. 51) with weekly time axis summarizes the patient's hospitalized course shown in FIG. 50 for the first five weeks, and illustrates his blood pressure and pulse rate after his discharge. Although he still had uncontrollable high blood pressure, he did not suffer tachycardial attacks.

Figure 52:
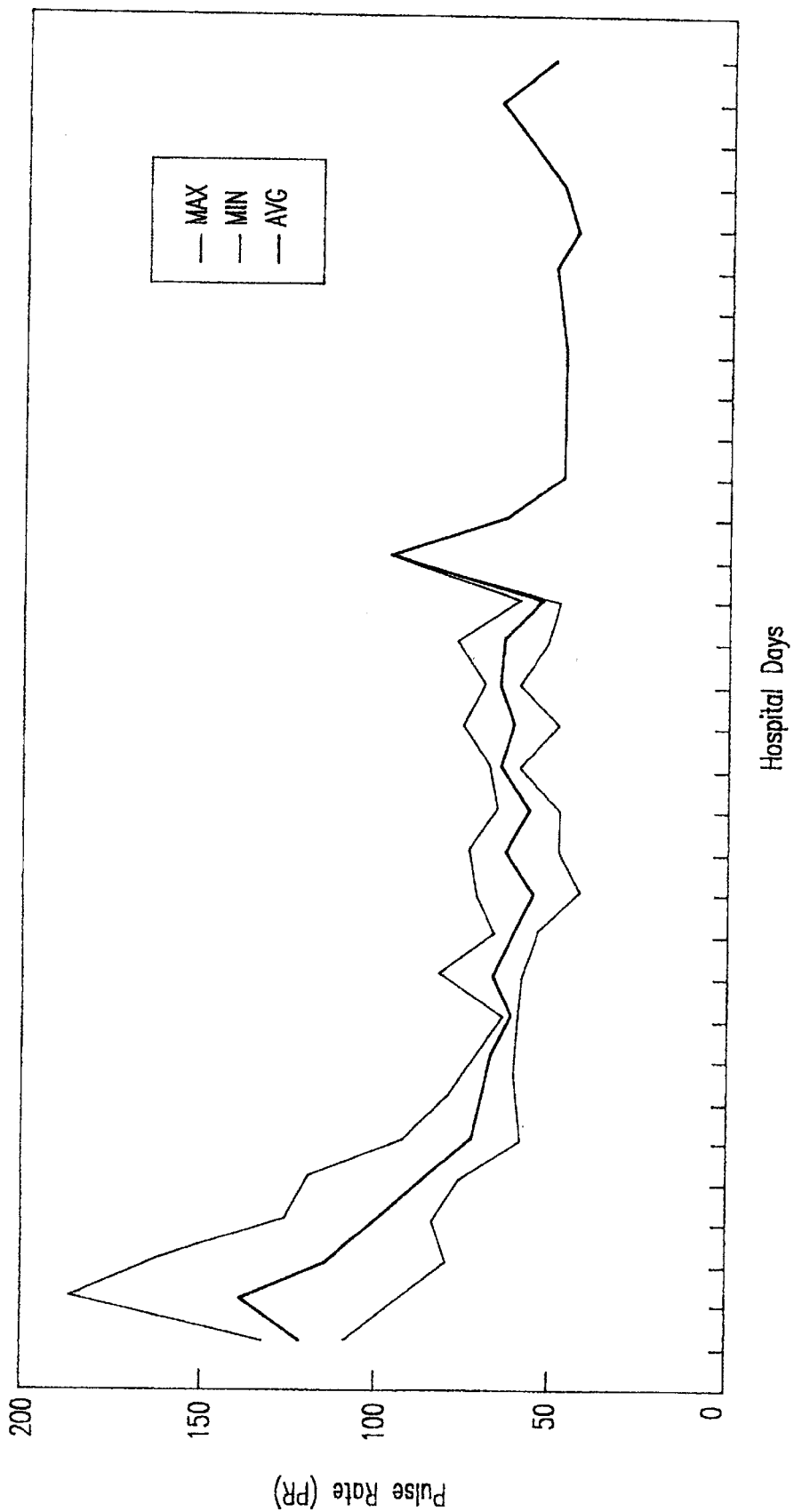
FIG. 52 is a simultaneous presentation of the average, maximum and minimum valves of medical information.

Another method of the display using the DBMS with NTA cooperating with the CMFCS is simultaneous presentation of the average, maximum and minimum of medical information in a single chart. In the process of the DBMS with NTA, information is compressed as well as generated. Some important information might be discarded because all data cannot be displayed in the single chart. However, by the presentation of the maximum and minimum values along with the average in the same time axis, clinical situations can be more comprehensibly displayed (FIG. 52). In certain circumstances, values of standard deviation or standard error could be used instead of the maximum and minimum values.

While this invention is particularly useful and adapted for daily medical practice, general medical studies, and especially drug trials, the concept of the invention is applicable to studies of other natural phenomena or other situations. The above description of the invention is of a preferred embodiment of the invention and modification may be made thereto without departing from the spirit and scope of the invention, which is defined in the appended claims.

What is claimed is:

1. A method of producing medical charts from data stored in database tables, said database tables comprising a structure of multiple nested time axes, comprising the steps of:
    monitoring patient conditions and taking measurements reflecting said patient conditions;
    entering data resulting from said measurements into an original database in a digital computer;
    determining a time interval;
    extracting records from said original database according to said time interval;
    calculating one or more values from the data in said records for said time interval;
    constructing a first progeny database table, said first progeny database table containing said values for a plurality of said time intervals; and
    constructing other progeny database tables with time axes different from the time axis of said first progeny database table, said other progeny database tables being constructed from said first progeny database table,
    wherein said first progeny database table and said other progeny database tables serve as input to a computed file medical chart system, said computed medical file chart system generating said medical charts showing changes in clinical data, and wherein said computed medical file chart system replaces missing values with interpolated values.

2. The method of producing medical charts according to claim 1, wherein said values comprise an average, a maximum, a minimum, and the number of extracted records for said time interval.

3. The method of producing medical charts according to claim 1,
wherein said patient conditions are collected directly from a patient by a monitoring machine, said monitoring machine transferring said patient conditions to said original database.

4. The method of producing medical charts according to claim 1, wherein said charts produced by said computed medical file chart system show changes in clinical data from said first progeny database.

5. The method of producing medical charts according to claim 1, further comprising the step of calculating a standard deviation for said data in said first progeny database and said other progeny databases.

6. The method of producing medical charts according to claim 1, further comprising the step of calculating a standard error for said data in said first progeny database and said other progeny databases.

7. The method of producing medical charts according to claim 1, further comprising the step of using said medical charts in connection with an epidemiological study.

8. The method of producing medical charts according to claim 1, further comprising the step of using said medical charts in connection with a study on the effectiveness of a new drug.

9. A computer memory for storing patient data for access by a computed medical file chart system, comprising:
a data structure stored in said memory, said data structure including information resident therein and forming a database used by said computed medical file chart system and including:
an original database comprising records, said records including information such as patient identification, date, time, and medical data related to a patient;
a first progeny database logically connected to said original database, said first progeny database comprising values such as the averages, maximums, minimums and numbers of records from a plurality of time intervals of said original database; and
a second progeny database, said second progeny database constructed from the averages, maximums, minimums and numbers of records of a plurality of time intervals from said first progeny database, wherein said second progeny database comprises values reflecting changes in clinical data and wherein missing values are replaced with interpolated values.

10. A computer memory according to claim 9, said computer memory further comprising multiple progeny databases, said multiple progeny databases being associated with particular time intervals.

11. A computer system for monitoring and reporting patient conditions comprising:
a first data portion comprising patient identification, date, time, and medical data relating to a patient;
a second data portion comprising values such as an average, a maximum, a minimum and the number of records from a particular time interval in said first data portion;
a third data portion comprising a database constructed from said averages, maximums, minimums and numbers of records from a plurality of time intervals from said second data portion; and
a fourth data portion comprising the averages, maximums, minimums and number of records from a plurality of time intervals of said third data portion, wherein said fourth data portion comprises values reflecting changes in clinical data and wherein missing values are replaced with interpolated values.

12. A computer program embodied on a computer readable medium for producing medical charts from database tables, said database tables containing multiple nested time axes, said computer program comprising:
a first source code segment, said first source code segment controlling monitoring devices and receiving data from said monitoring devices;
a second source code segment recording said data into an original database;
a third source code segment determining a time interval and extracting records from said original database according to said time interval;
a fourth code segment calculating values such as an average, a maximum, a minimum and the number of extracted records for said time interval;
a fifth code segment constructing a progeny database table, said progeny database table containing the averages, maximums, minimums and number of extracted records for a plurality of said time intervals; and
a sixth code segment using said progeny database table to construct other progeny database tables with other time axes, wherein said other progeny database tables comprise database values reflecting changes in clinical data and wherein missing values are replaced with interpolated values.

13. A computer readable medium for causing a computer to produce medical charts from database tables, said database tables containing multiple nested time axes, comprising:
a computer readable storage medium;
a computer program stored on said medium, said computer program having an interface module, said interface module monitoring machines which collect data from a patient;
said monitoring module further collecting said data and routing said data to an original database;
said computer program further having an extraction module, said extraction module determining a time interval and extracting records from said original database according to said time interval;
said computer program further comprising a calculation module, said calculation module calculating values such as an average, maximum, minimum and number of extracted records for said time interval;
said computer program further comprising a construction module, said construction module constructing a progeny database table, said progeny database table containing the averages, maximums, minimums and numbers of extracted records for a plurality of said time intervals; and
said computer program further comprising a progeny database table module, said progeny database table module constructing other progeny database tables with other time axes, wherein said other progeny database tables comprise values reflecting changes in clinical data and wherein missing values are replaced with interpolated values.

* * * * *